(12) United States Patent
Kung et al.

(10) Patent No.: US 8,080,556 B2
(45) Date of Patent: Dec. 20, 2011

(54) 2-AMINO PYRIMIDINE COMPOUNDS AS POTENT HSP-90 INHIBITORS

(75) Inventors: Pei-Pei Kung, San Diego, CA (US); Jerry Jialun Meng, San Diego, CA (US)

(73) Assignee: Pfizer Inc., New York, NY (US)

( * ) Notice: Subject to any disclaimer, the term of this patent is extended or adjusted under 35 U.S.C. 154(b) by 94 days.

(21) Appl. No.: 12/535,468

(22) Filed: Aug. 4, 2009

(65) Prior Publication Data

US 2010/0041681 A1 Feb. 18, 2010

Related U.S. Application Data

(60) Provisional application No. 61/088,599, filed on Aug. 13, 2008.

(51) Int. Cl.
*A01N 43/90* (2006.01)
*A61K 31/519* (2006.01)
*C07D 487/00* (2006.01)
(52) U.S. Cl. .................. 514/265.1; 544/280
(58) Field of Classification Search .................. None
See application file for complete search history.

(56) References Cited

U.S. PATENT DOCUMENTS

2010/0093696 A1* 4/2010 Bennett et al. ........... 514/210.21

FOREIGN PATENT DOCUMENTS

| WO | WO03062225 | 7/2003 |
|---|---|---|
| WO | WO2006105372 | 10/2006 |
| WO | WO2006117669 | 11/2006 |
| WO | WO2006118598 | 11/2006 |
| WO | WO2008044029 | 4/2008 |
| WO | WO2008096218 | 8/2008 |

OTHER PUBLICATIONS http://www.plosone.org/article/info%3Adoi%2F10.1371%2Fjournal.pone.0001722, last accessed omn Dec. 21, 2010.*
Holstein, I. et al., "Inhibition of Signal Transduction by the Hsp90 Inhibitor 17-Allylamino-17-demethoxygeldanamycin Results in Cytostasis and Apoptosis," *Cancer Research*, 2001, 61, 4003-4009.
Jolly, C. et al., "Role of the Heat Shock Response and Molecular Chaperones in Oncogenesis and Cell Death," *Journal of the National Cancer Institute*, 2000, 92:19, 1564-1572.
Martin, K. et al., "Linking Gene Expression Patterns to Therapeutic Groups in Breast Cancer," *Cancer Research*, 2000, 60, 2232-2238.

Xu, Y. et al., "Heat-shock protein hsp90 governs the activity of pp60$^{v-src}$ kinase," *Proceedings of National Academy Sciences*, 1993, 90, 7074-7078.
Young, J. et al., "Hsp90: A Specialized but Essential Protein-Folding Tool," *Journal of Cell Biology*, 2001, 154, 267-273.
Benderitter, P., et al., "2-Amino-6-iodo-4-tosyloxypyrimidine: a Versatile Key Intermediate for Regioselective Functionalization of 2-aminopyrimidines in 4- and 6-positions," Tetrahedron, 2007, 12465-12470, vol. 63.
Dorwald, F., "Side Reactions in Organic Synthesis," Wiley-VCH Verlag GmbH & Co.KGaA, Weinheim, 2005, Preface, p. IX.
Gallegos Ruiz, M., et al., "Integration of Gene Dosage and Gene Expression in Non-Small Cell Lung Cancer, Identification of Hsp90 as Potential Target," PLoS ONE, 2008, 1-8, vol. 3, No. 3.
Hostein, I., et al., "Inhibition of Signal Transduction by the Hsp90 Inhibitor 17-Allylamino-17-demethoxygeldanamycin Results in Cytostasis and Apoptosis," Cancer Research, 2001, 4003-4009, vol. 61.
Jolly, C., et al., "Role of the Heat Shock Response and Molecular Chaperones in Oncogenesis and Cell Death," Journal of the National Cancer Institute, 2000, 1564-1572, vol. 92, No. 19.
Martin, K, et al., "Linking Gene Expression Patterns to Therapeutic Groups in Breast Cancer," Cancer Research, 2000, 2232-2238, vol. 60.
Xu, Y., et al., "Heat-shock Protein Hsp90 Governs the Activity of pp60v-src Kinase," Proceedings of the National Academy of Sciences, 1993, 7074-7078, vol. 90.
Young, J., et al., "Hsp90: A Specialized but Essential Protein-Folding Tool," Journal of Cell Biology, 2001, 267-273, vol. 154, No. 2.

* cited by examiner

*Primary Examiner* — Jeffrey Murray
(74) *Attorney, Agent, or Firm* — Suzanne M. Bates; Ye Hua; Stephen D. Prodnuk

(57) ABSTRACT

The present invention is directed to compounds of formula (I),

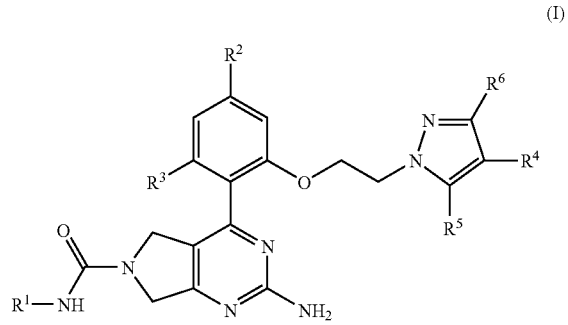

or pharmaceutically acceptable salts thereof, their synthesis, and their use as HSP-90 inhibitors.

16 Claims, No Drawings

2-AMINO PYRIMIDINE COMPOUNDS AS POTENT HSP-90 INHIBITORS

This application claims the benefit of U.S. Provisional Patent Application No. 61/088,599, filed Aug. 13, 2008, the disclosure of which is incorporated herein by reference in its entirety.

FIELD OF THE INVENTION

The present invention is directed to compounds, and pharmaceutically acceptable salts and solvates thereof, their synthesis, and their use as modulators or inhibitors of HSP-90. The compounds of the present invention are useful for modulating (e.g. inhibiting) HSP-90 activity and for treating diseases or conditions mediated by HSP-90, such as for example, disease states associated with abnormal cell growth such as cancer.

BACKGROUND

Molecular chaperones play important roles in cellular function by ensuring proper folding of proteins upon synthesis as well as their refolding under conditions of denaturing stress. By regulating the balance between protein synthesis and degradation, molecular chaperones are a significant part of the cellular response to stress. In addition, by regulating the proper folding of various cellular proteins, chaperones play an important role in regulating cellular functions such as cell proliferation and apoptosis. (See, e.g. Jolly, et al., *J. Natl. Cancer Inst.* 92: 1564-1572 (2000)). Heat shock proteins (HSPs) are a class of chaperones that accumulate in the cell in response to various environmental stresses, such as heat shock, oxidative stress, or the presence of alcohols or heavy metals. In addition to their role in protecting the cell from such environmental stresses, HSPs may also play a significant role as chaperones for a variety of cellular proteins under stress-free conditions. Members of the HSP family are classified according to their molecular weight (e.g. HSP-27, HSP-70, and HSP-90). Evidence of differential expression of HSPs in various stages of tumor progression suggests HSPs play a role in cancer. (See, e.g. Martin, et al., *Cancer Res.* 60:2232-2238 (2000)).

HSP-90 is a homodimer with ATPase activity and functions in a series of complex interactions with a variety of substrate proteins (Young, et al., *J. Cell Biol.* 154: 267-273 (2001)). HSP-90 is unique with regard to other chaperones, however, since most of its known substrate proteins are signal transduction proteins. Thus, HSP-90 plays an essential role in regulating cellular signal transduction networks. (See, e.g. Xu, et al., *Proc. Natl. Acad. Sci.* 90:7074-7078 (1993)). In particular, substrate proteins of HSP-90 include many mutated or over-expressed proteins implicated in cancer such as p53, Bcr-Abl kinase, Raf-1 kinase, Akt kinase, Npm-Alk kinase p185$^{ErbB2}$ transmembrane kinase, Cdk4, Cdk6, Wee1 (a cell cycle-dependent kinase), HER2/Neu (ErbB2), and hypoxia inducible factor-1α (HIF-1α). Thus inhibition of HSP-90 results in selective degradation of these important signaling proteins involved in apoptosis, cell proliferation, and cell cycle regulation (Holstein, et al., *Cancer Res.* 61:4003-4009 (2001)). Accordingly, HSP-90 is an attractive therapeutic target because of the important roles played by these signaling proteins in disease states involving abnormal cell growth, such as cancer. It is thus desirable to discover and develop new inhibitors of HSP-90 activity that can provide a therapeutic benefit to patients suffering from disease states related to abnormal cell growth such as cancer.

SUMMARY

In one embodiment, the invention provides a compound of formula (I),

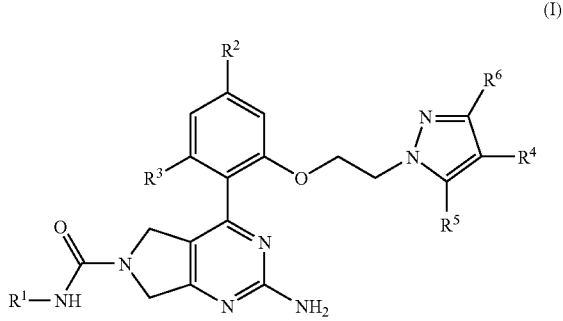

or a pharmaceutically acceptable salt thereof, wherein:

$R^1$ is selected from the group consisting of $C_1$-$C_6$ alkyl, $C_1$-$C_6$ alkyl substituted with 1 to 6 fluorine, $C_1$-$C_6$ alkyl substituted with 1 to 2 chlorine and up to six fluorine, $C_3$-$C_8$ cycloalkyl, and $C_3$-$C_8$ cycloalkyl substituted with 1 to 6 groups independently selected from fluorine, chlorine and $C_1$-$C_3$ alkyl;

$R^2$ and $R^3$ are each independently selected from the group consisting of chlorine, fluorine, $C_1$-$C_3$ alkyl and $C_1$-$C_3$ alkyl substituted with 1 to 6 fluorine;

$R^4$ is selected from the group consisting of hydrogen, fluorine, chlorine, bromine, —CN, $C_1$-$C_3$ alkyl and $C_1$-$C_3$ alkyl substituted with 1 to 6 fluorine;

$R^5$ and $R^6$ are each independently selected from the group consisting of hydrogen, fluorine, chlorine, bromine, —CN, $C_1$-$C_3$ alkyl and $C_1$-$C_3$ alkyl substituted with 1 to 6 fluorine;

provided that (1) when $R^4$, $R^5$ and $R^6$ are all hydrogen, then $R^2$ and $R^3$ are not both chlorine; and (2) the compound of formula I is not any of the following compounds,

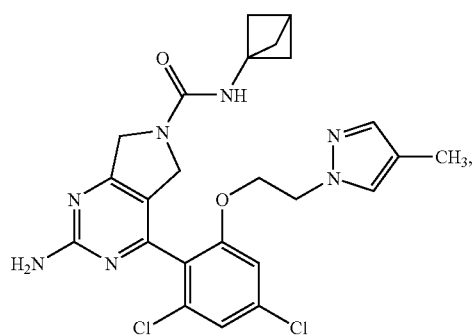

-continued

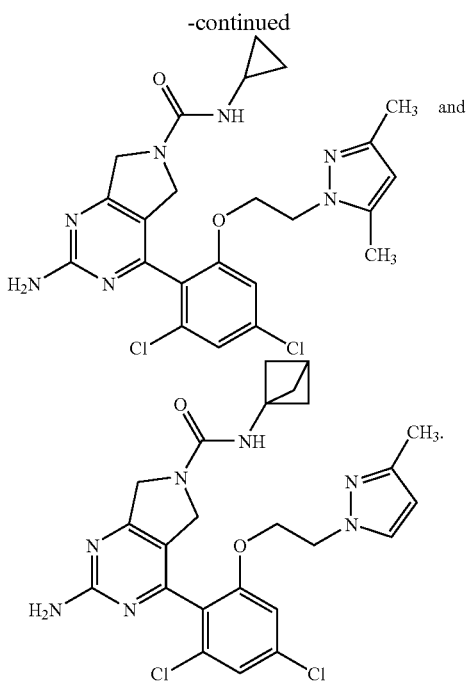

In a preferred aspect of the embodiment, and in combination with any other preferred aspects not inconsistent, $R^4$ is hydrogen, $R^5$ is hydrogen, $R^6$ is hydrogen, $R^3$ is selected from the group consisting of fluorine, $C_1$-$C_3$ alkyl and $C_1$-$C_3$ alkyl substituted with 1 to 6 fluorine. Preferably, $R^3$ is $C_1$-$C_3$ alkyl.

In another preferred aspect of the embodiment, and in combination with any other preferred aspects not inconsistent, $R^4$ is hydrogen, $R^5$ is hydrogen, $R^6$ is hydrogen, and $R^2$ is selected from the group consisting of fluorine, $C_1$-$C_3$ alkyl and $C_1$-$C_3$ alkyl substituted with 1 to 6 fluorine.

In another preferred aspect of the embodiment, and in combination with any other preferred aspects not inconsistent, $R^4$ is selected from fluorine, chlorine, $C_2$-$C_3$ alkyl and $C_1$-$C_3$ alkyl substituted with 1 to 6 fluorine. Preferably, $R^4$ is selected from fluorine and chlorine. More preferably, $R^4$ is fluorine.

In another preferred aspect of the embodiment, and in combination with any other preferred aspects not inconsistent, $R^4$ is fluorine or chlorine, $R^5$ is hydrogen, and $R^6$ is hydrogen. Preferably, $R^4$ is fluorine, and $R^5$ and $R^6$ are both hydrogen.

In another preferred aspect of the embodiment, and in combination with any other preferred aspects not inconsistent, $R^4$ is fluorine or chlorine, $R^5$ is hydrogen, $R^6$ is hydrogen, $R^2$ is methyl or chlorine, and $R^3$ is methyl or chlorine.

In another preferred aspect of the embodiment, and in combination with any other preferred aspects not inconsistent, $R^5$ is $C_1$-$C_3$ alkyl substituted with 1 to 6 fluorine.

In another preferred aspect of the embodiment, and in combination with any other preferred aspects not inconsistent, $R^6$ is $C_1$-$C_3$ alkyl substituted with 1 to 6 fluorine.

In another preferred aspect of the embodiment, and in combination with any other preferred aspects not inconsistent, $R^1$ is selected from the group consisting of cyclopropyl, cyclobutyl, bicyclo[1.1.1]pent-1-yl, and $C_1$-$C_6$ alkyl substituted with 1 to 6 fluorine.

In another preferred aspect of the embodiment, and in combination with any other preferred aspects not inconsistent, $R^1$ is $C_3$-$C_8$ cycloalkyl or $C_3$-$C_8$ cycloalkyl substituted with 1 to 6 groups selected from fluorine, chlorine and $C_1$-$C_3$ alkyl.

In another preferred aspect of the embodiment, and in combination with any other preferred aspects not inconsistent, $R^1$ is $C_1$-$C_6$ alkyl, $C_1$-$C_6$ alkyl substituted with 1 to 6 fluorine, or $C_1$-$C_6$ alkyl substituted with 1 to 2 chlorine and up to 6 fluorine.

In another preferred aspect of the embodiment, and in combination with any other preferred aspects not inconsistent, $R^2$ is chlorine and $R^3$ is chlorine.

In another preferred aspect of the embodiment, and in combination with any other preferred aspects not inconsistent, $R^2$ is chlorine and $R^3$ is $C_1$-$C_3$ alkyl. In another preferred aspect of the embodiment, and in combination with any other preferred aspects not inconsistent, $R^4$ is fluorine or chlorine, $R^5$ is hydrogen, $R^6$ is hydrogen, $R^2$ is methyl or chlorine, $R^3$ is methyl or chlorine, $R^1$ is selected from the group consisting of cyclopropyl, cyclobutyl, bicyclo[1.1.1]pent-1-yl, and $C_1$-$C_6$ alkyl substituted with 1 to 6 fluorine. Preferably, $R^4$ is fluorine, $R^2$ is chlorine and $R^3$ is chlorine. More preferably, $R^4$ is fluorine, $R^2$ is chlorine and $R^3$ is methyl.

In another embodiment, the invention provides a compound of formula I,

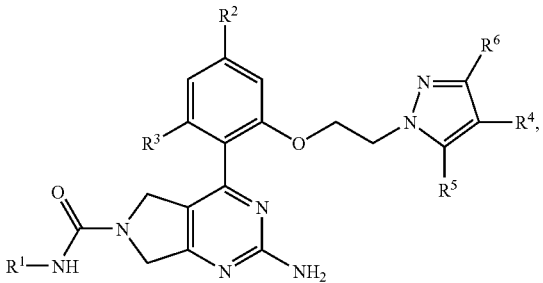

(I)

wherein:
$R^1$ is selected from the group consisting of $C_1$-$C_6$ alkyl, $C_1$-$C_6$ alkyl substituted with 1 to 6 fluorine, $C_1$-$C_6$ alkyl substituted with 1 to 2 chlorine and up to 6 fluorine, $C_3$-$C_8$ cycloalkyl, and $C_3$-$C_8$ cycloalkyl substituted with 1 to 6 groups independently selected from fluorine, chlorine and $C_1$-$C_3$ alkyl;

$R^2$ and $R^3$ are each independently selected from the group consisting of chlorine, fluorine, $C_1$-$C_3$ alkyl and $C_1$-$C_3$ alkyl substituted with 1 to 6 fluorine;

$R^4$ is selected from fluorine, chlorine, $C_2$-$C_3$ alkyl and $C_1$-$C_3$ alkyl substituted with 1 to 6 fluorine. Preferably, $R^4$ is selected from fluorine and chlorine. More preferably, $R^4$ is fluorine.

$R^5$ and $R^6$ are each independently selected from the group consisting of hydrogen, fluorine, chlorine, bromine, —CN, $C_1$-$C_3$ alkyl, $C_1$-$C_3$ alkyl substituted with 1 to 6 fluorine;

or a pharmaceutically acceptable salt thereof.

In one preferred aspect of the embodiment, and in combination with any other preferred aspects not inconsistent, $R^4$ is fluorine or chlorine, $R^5$ is hydrogen, and $R^6$ is hydrogen. More preferably, $R^4$ is fluorine, and $R^5$ and $R^6$ are both hydrogen.

In another preferred aspect of the embodiment, and in combination with any other preferred aspects not inconsistent, $R^4$ is fluorine or chlorine, $R^5$ is hydrogen, $R^6$ is hydrogen, $R^2$ is methyl or chlorine, and $R^3$ is methyl or chlorine.

In another preferred aspect of the embodiment, and in combination with any other preferred aspects not inconsistent, $R^5$ is $C_1$-$C_3$ alkyl substituted with 1 to 6 fluorine.

In another preferred aspect of the embodiment, and in combination with any other preferred aspects not inconsistent, $R^6$ is $C_1$-$C_3$ alkyl substituted with 1 to 6 fluorine.

In another preferred aspect of the embodiment, and in combination with any other preferred aspects not inconsistent, $R^1$ is selected from the group consisting of cyclopropyl, cyclobutyl, bicyclo[1.1.1]pent-1-yl, and $C_1$-$C_6$ alkyl substituted with 1 to 6 fluorine.

In another preferred aspect of the embodiment, and in combination with any other preferred aspects not inconsistent, $R^1$ is $C_3$-$C_8$ cycloalkyl or $C_3$-$C_8$ cycloalkyl substituted with 1 to 6 groups independently selected from fluorine, chlorine and $C_1$-$C_3$ alkyl.

In another preferred aspect of the embodiment, and in combination with any other preferred aspects not inconsistent, $R^1$ is $C_1$-$C_6$ alkyl, $C_1$-$C_6$ alkyl substituted with 1 to 6 fluorine, $C_1$-$C_6$ alkyl substituted with 1 to 2 chlorine and up to six fluorine.

In another preferred aspect of the embodiment, and in combination with any other preferred aspects not inconsistent, $R^2$ is chlorine and $R^3$ is chlorine.

In another preferred aspect of the embodiment, and in combination with any other preferred aspects not inconsistent, $R^2$ is chlorine and $R^3$ is $C_1$-$C_3$ alkyl. In another preferred aspect of the embodiment, and in combination with any other preferred aspects not inconsistent, $R^4$ is fluorine or chlorine, $R^5$ is hydrogen, $R^6$ is hydrogen, $R^2$ is methyl or chlorine, $R^3$ is methyl or chlorine and, $R^1$ is selected from the group consisting of cyclopropyl, cyclobutyl, bicyclo[1.1.1]pent-1-yl, and $C_1$-$C_6$ alkyl substituted with 1 to 6 fluorine. Preferably, $R^4$ is fluorine, $R^2$ is chlorine and $R^3$ is chlorine. More preferably, $R^4$ is fluorine, $R^2$ is chlorine and $R^3$ is methyl.

In another embodiment, the invention provides a compound selected from the group consisting of

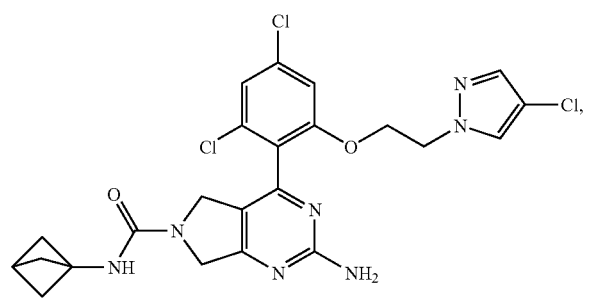

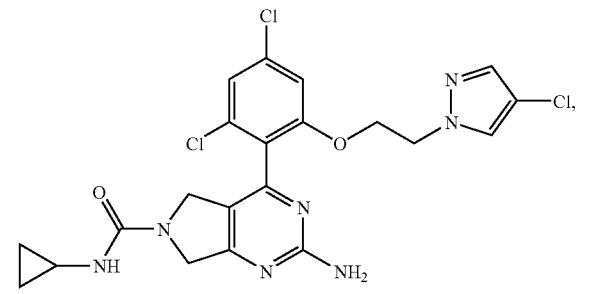

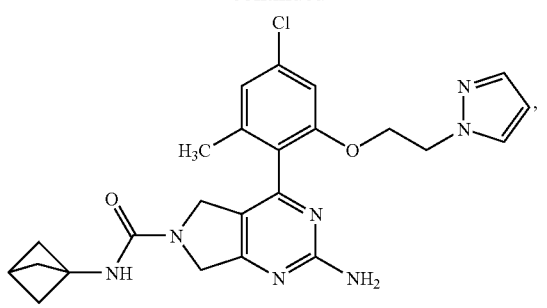

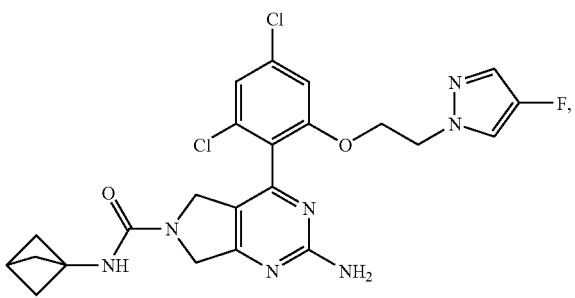

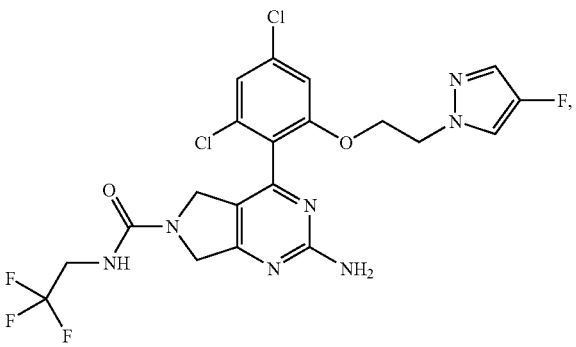

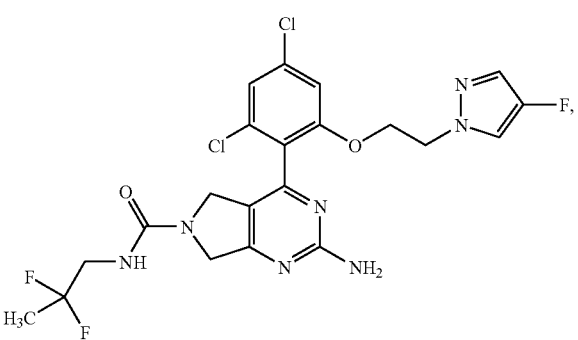

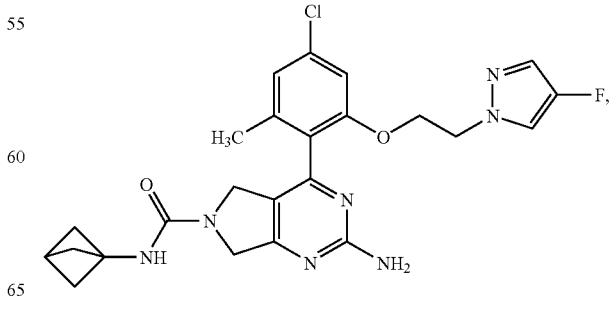

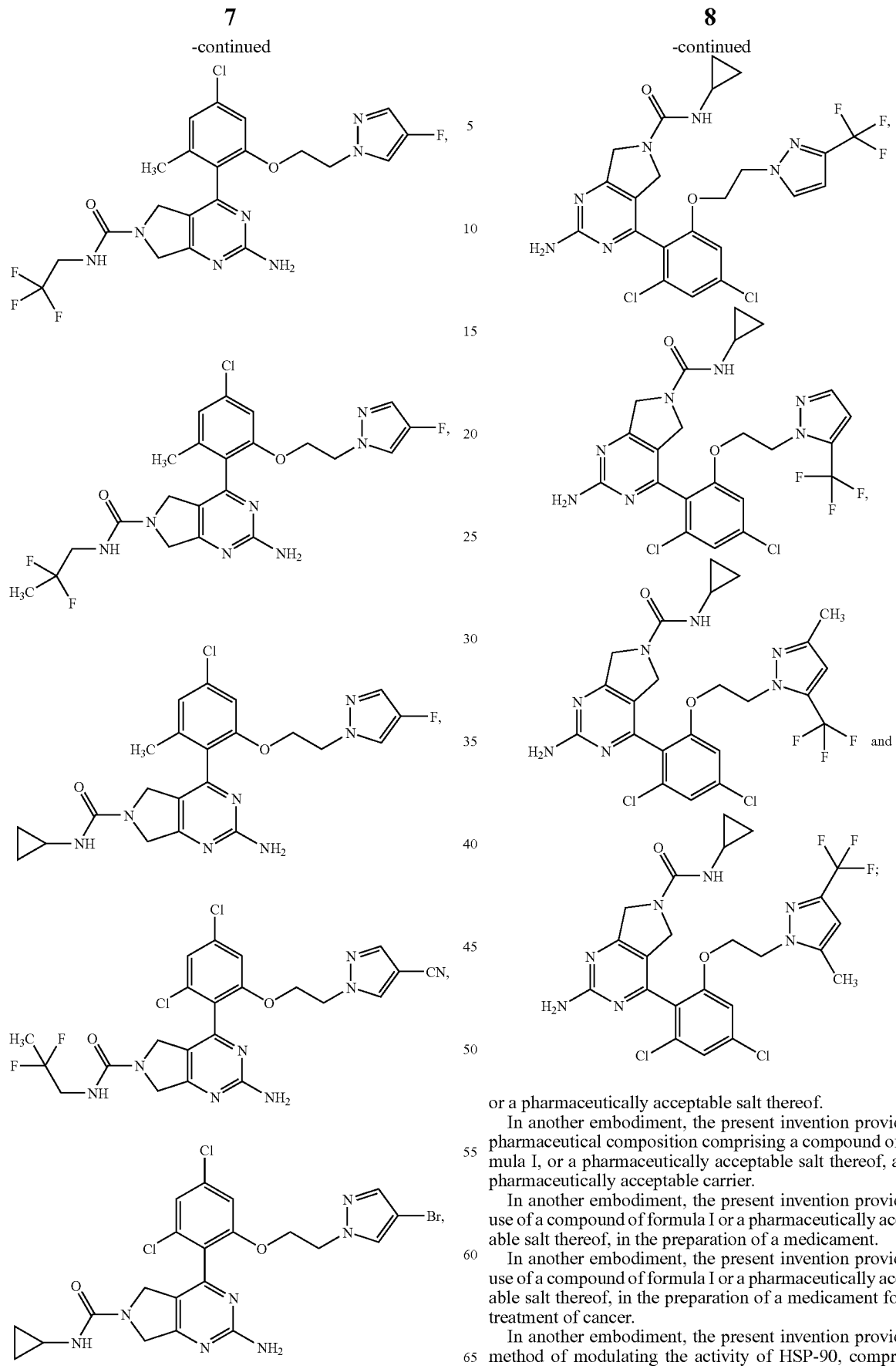

or a pharmaceutically acceptable salt thereof.

In another embodiment, the present invention provides a pharmaceutical composition comprising a compound of formula I, or a pharmaceutically acceptable salt thereof, and a pharmaceutically acceptable carrier.

In another embodiment, the present invention provides a use of a compound of formula I or a pharmaceutically acceptable salt thereof, in the preparation of a medicament.

In another embodiment, the present invention provides a use of a compound of formula I or a pharmaceutically acceptable salt thereof, in the preparation of a medicament for the treatment of cancer.

In another embodiment, the present invention provides a method of modulating the activity of HSP-90, comprising contacting a cell with a compound of formula I or a pharmaceutically acceptable salt thereof.

In another embodiment, the invention provides a combination of the compound or salt of Formula I and a further therapeutic agent. In one aspect of this embodiment, the combination is used for the treatment of abnormal cell growth, preferably cancer.

This invention also relates to a method for the treatment of abnormal cell growth in a mammal, including a human, comprising administering to said mammal an amount of a compound of the Formula I, as defined above, or a pharmaceutically acceptable salt or solvate thereof, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non-hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, and retinoblastoma, or a combination of one or more of the foregoing cancers.

In another embodiment of said method, said abnormal cell growth is a benign proliferative disease, including, but not limited to, psoriasis, benign prostatic hypertrophy and restinosis.

In a preferred embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-hodgkin's lymphoma, and spinal axis tumors, or a combination of one or more of the foregoing cancers.

In another preferred embodiment of the present invention the cancer is selected from lung cancer (NSCLC and SCLC), ovarian cancer, colon cancer, rectal cancer, and cancer of the anal region, or a combination of one or more of the foregoing cancers.

In a more preferred embodiment of the present invention the cancer is selected from lung cancer (NSCLC and SCLC), ovarian cancer, colon cancer, and rectal cancer, or a combination of one or more of the foregoing cancers.

In another embodiment of said method, said abnormal cell growth is a benign proliferative disease, including, but not limited to, psoriasis, benign prostatic hypertrophy and restinosis.

This invention also relates to a pharmaceutical composition for the treatment of abnormal cell growth in a mammal, including a human, comprising an amount of a compound of the formula I, as defined above, or a pharmaceutically acceptable salt thereof, that is effective in treating abnormal cell growth, and a pharmaceutically acceptable carrier. In one embodiment of said composition, said abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, and retinoblastoma, or a combination of one or more of the foregoing cancers. In another embodiment of said pharmaceutical composition, said abnormal cell growth is a benign proliferative disease, including, but not limited to, psoriasis, benign prostatic hypertrophy and restinosis.

As used herein, the symbol [------] when incorporated into the chemical structure of a substituent means that the atom to which [------] is attached is the point of attachment of that substitutent to some position on another molecule. For example, X in the hypothetical molecule $CH_3CH_2$—X might be defined as X is

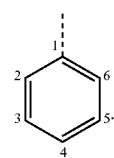

In which case, the placement of [------] attached to the arbitrarily numbered position C-1, means that C-1 of the phenyl ring is attached to the methylene carbon.

"$C_m$-$C_n$ alkyl", wherein m is an integer of 1-19, n is an integer of 2 to 20 and n>m, refers to a straight chain or branched saturated hydrocarbon radical having from m to n carbon atoms, wherein n is an integer of 2 to 20. Examples of $C_m$-$C_n$ alkyl groups include, but are not limited to methyl, ethyl, propyl, isopropyl, butyl, sec-butyl, iso-butyl, tert-butyl, pentyl, neo-pentyl, sec-pentyl, hexyl, heptyl, octyl, and the like, including substituted forms thereof. Further, the term "alkyl" refers to a straight chain or branched saturated hydrocarbon radical of 1 to 20 carbon atoms, or 1 to 12 carbon atoms, or 1 to 8 carbon atoms, or 1 to 6 carbon atoms, or 1 to 4 carbon atoms. Alkyl may be may be unsubstituted or further substituted by at least one substituent.

"$C_m$-$C_n$ cycloalkyl", wherein m is an integer of 3-19, n is an integer of 4 to 20 and n>m, refers to a cyclic saturated hydrocarbon radical having from m to n carbon atoms. A cycloalkyl group may be monocyclic and where permissible may be bicyclic or polycyclic. A cycloalkyl may also be a spirocyclic. Illustrative examples of cycloalkyl are derived from, but not limited to, the following:

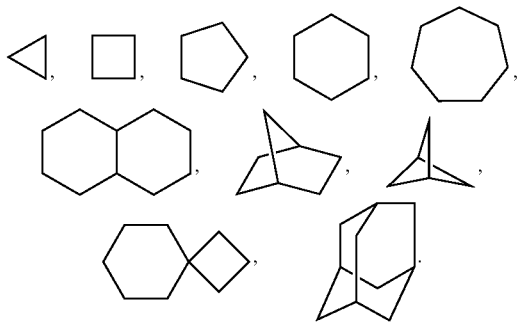

"$C_m$-$C_n$ Alkoxy" or "$C_m$-$C_n$ alkoxyl" refers to —O—($C_m$-$C_n$ alkyl) Wherein ($C_m$-$C_n$ alkyl) is as defined previously in this section.

"Amino" refers to —$NH_2$.

When a group is "optionally substituted" or "optionally further substituted" by some substituents, it means a carbon or a nitrogen atom of this group wherein one or more hydrogen atoms are attached to the carbon or nitrogen atom, such carbon or nitrogen atom is optionally substituted by some other substituents. For example, "R is H, $C_1$-$C_3$ alkyl or phenyl, and R is optionally further substituted by 1-3 groups selected from —F, oxo and $C_1$-$C_3$ perfluoroalkyl", means that R is 1) H (when R is H, R cannot be further substituted); 2) $C_1$-$C_3$ alkyl optionally further substituted by 1-3 groups selected from —F, oxo and $C_1$-$C_3$ perfluoroalkyl; and 3) phenyl optionally further substituted by 1-3 groups selected from —F and $C_1$-$C_3$ perfluoroalkyl. Optional substitution of phenyl by oxo does not apply when R is phenyl because no single atom of the phenyl group possess two hydrogen atoms to be substituted by oxo, i.e. =O bond. When a group is further substituted by a "-($C_1$-$C_4$ alkylene)-", it means the "-($C_1$-$C_4$ alkylene)-", together with the nitrogen atom or the carbon atom of the group to which "$C_1$-$C_4$ alkylene" is attached, form a carbo or hetero spirocycle.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism, such as a mammal, including a human.

As used herein, a "physiologically/pharmaceutically acceptable carrier" refers to a carrier or diluent that does not cause significant irritation to an organism such as a mammal, including a human and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts that retain the biological effectiveness and properties of the parent compound. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Contacting" refers to bringing a compound of the present teachings and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, can be determined. For cells outside a organism, multiple methods exist that are known to those skilled in the art, to get the PKs in contact with the compounds including, but not limited to, direct cell microinjection and numerous transmembrane carrier techniques.

"PK related disorder," "PK driven disorder," and "abnormal PK activity" all refer to a condition characterized by inappropriate, i.e., under or, over, PK catalytic activity, where the particular PK can be an RTK, a CTK or an STK. Inappropriate catalytic activity can arise from: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard to cancer, these terms mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

DETAILED DESCRIPTION

The compounds of the current invention, i.e., the compounds of formula I, can be made following the method of Examples 1-16. The following reaction Schemes 1-3 will enable one of ordinary skill in the art to make the compound of formula I.

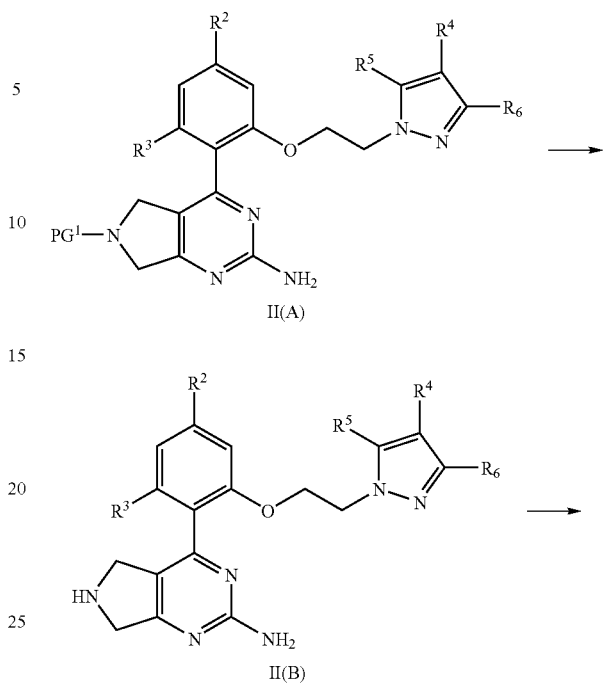

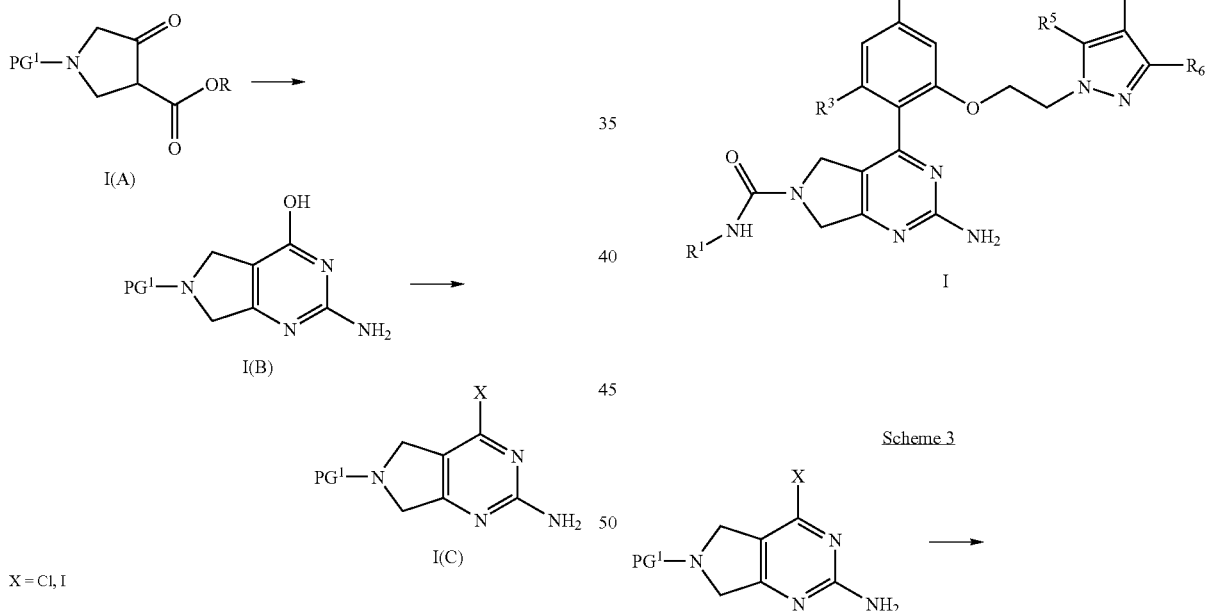

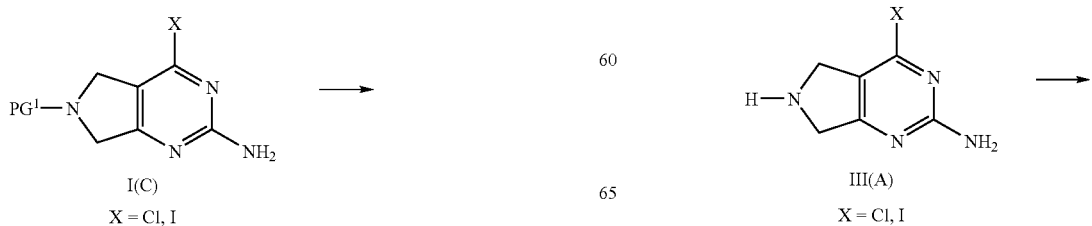

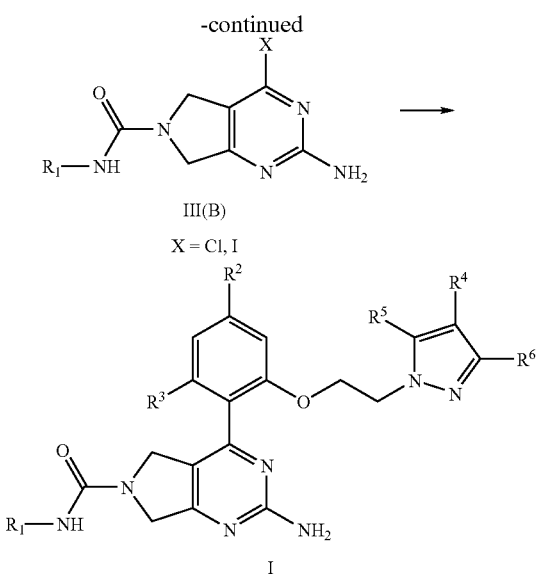

Scheme 1 illustrates the synthesis of intermediate I(C) used to make compounds of formula I. The beta keto ester I(A) can be prepared based on a known procedures (see, e.g. Viscontini and Buhler *Helvetica Chimica Acta,* 50(5): 1289-93; (1967), Rosowsky et. al. *J. Heterocyclic Chem.,* 26: 509-16 (1989)). PG$^1$, the nitrogen protecting group, can be selected for compatability with subsequent chemistry. Protecting groups and general considerations for their use are described in T. Greene and P. Wuts, "Protective Groups in Organic Synthesis", 3$^{rd}$ Edition 1999, John Wiley & Sons and are well known to those skilled in the art. Compound I(A) is condensed with guanidine to give compound I(B). This can typically be done by heating compound I(A) with guanidine or guanidine equivalent a protic solvent. A typical reaction condition would be to reflux compound I(A) with guandidine carbonate in tert-butanol as a solvent. Conversion of the hydroxyl group of compound I(B) to chloro or iodo gives I(C). This can typically be done by heating compound I(B) with POCl$_3$ in an aprotic solvent. A typical reaction condition would be to reflux compound I(B) together with excess POCl$_3$ either neat or in dry acetonitrile as solvent.

Scheme 2 illustrates the route through which compounds of formula I can be made from intermediate I(C). In Scheme 2, the chloro/iodo group of compound I(C) is replaced by a trisubstituted phenyl group to give compound II(A). The displacement of the chloro leaving group of compound I(C) by the trisubstituted phenyl group to give compound II(A) can be carried out using cross coupling methodology utilizing Suzuki, Stille, Negishi or similar conditions. A typical cross coupling reaction for the transformation of compound I(C) to compound II(A) would be to treat compound I(C) with a boronic acid or ester in the presence of a base such as sodium carbonate and Pd(0) catalyst in a solvent mixture such as water and 1,4-dioxane to give compound II(A). The nitrogen protecting group, PG$^1$, of compound II(A) is then removed to give compound II(B). When PG$^1$ forms an ethyl carbamate protecting group, removing of PG$^1$ can typically be done, by refluxing compound II(A) with trimethylsilyliodide in a solvent such as CH$_3$CN. Alternatively HBr in acetic acid or KOH in isopropanol can also be used to remove the ethyl carbamate protecting group. When PG$^1$ is a tert-butyl carbamate protecting group, removing of PG$^1$ can be done by treating compound II(A) with hydrogen chloride in a solvent such as 1,4-dioxane. A typical condition for the transformation of compound II(A) to compound II(B) is to treat compound II(A) with TMSI (10-20 equivalents, 4M in 1,4-dioxane) to give compound II(B). The dihydropyrrolo amino moiety of compound II(B) then acts as a nucleophile in reactions with an electrophilic R$^1$—NH—CO moiety to give compound 1. This nucleophilic reaction can be acylation and other reactions applicable to secondary alkyl amines. A typical acylation reaction condition is to react compound II(B) with an R$^1$ isocyanate or isocyanate equivalent moiety in the presence of TEA to give compound I as a urea. A method to prepare isocyanate equivalent is to form a adduct of CDI (1,1'-carbonyldiimidazole) with different amines. The CDI adduct can then react with compound II(B) to give compound I in the presence of TEA in DMF at elevated temperature.

Scheme 3 illustrates another route through which compounds of formula I can be made from intermediate I(C). In Scheme 3 when PG$^1$ is an ethyl carbamate protecting group, PG$^1$ of compound I(C) is removed with concurrent conversion of chloro to iodo in one step. This can typically be carried out by treating compound I(C) with TMSI at elevated temperature or with hydrogen chloride at room temperature in an aprotic solvent. A typical reaction condition is to reflux compound I(C) in CH$_3$CN with five equivalents of TMSI. Following a methanol quench, compound III(A) is obtained as an HI salt. The dihydropyrrolo amino moiety of compound III(A) then reacts, as a nucleophile, with an electrophilic R$^1$ moiety to give compound III(B). This nucleophilic reaction can be acylation and other reactions applicable to secondary alkyl amines. A typical acylation reaction condition is to react compound III(A) with an R$^1$ isocyanate or isocyanate equivalent moiety in the presence of TEA to give compound III(B) as a urea. A method to prepare isocyanate equivalent is to form a adduct of CDI (1,1'-carbonyldiimidazole) with different amines. The CDI adduct can then react with compound II(B) to give compound I in the presence of TEA in DMF at elevated temperature. The iodo group of compound III(B) is then displaced by the trisubstituted phenyl piece using cross coupling methodology to give compound 1. This reaction can typically be carried out using Suzuki, Stille, Negishi or similar conditions. A typical cross coupling reaction for the transformation of compound III(B) to compound I would be to treat compound III(B) with a boronic acid or ester in the presence of a base such as sodium carbonate and Pd(0) catalyst in a solvent mixture such as water and 1,4-dioxane to give compound 1.

The compounds of the present invention may have asymmetric carbon atoms. The carbon-carbon bonds of the compounds of the present invention may be depicted herein using a solid line (-), a solid wedge (▬), or a dotted wedge (⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization. Where structural isomers are interconvertible via a low energy barrier, tautomeric isomerism ('tautomerism') can occur. This can take the form of proton tautomerism in compounds of the present invention containing, for example, an imino, keto, or oxime group, or so-called valence tautomerism in compounds which contain an aromatic moiety. It follows that a single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In the case of compounds that are solids, it is understood by those skilled in the art that the inventive compounds and salts may exist in different crystalline or polymorphic forms, or in an amorphous form, all of which are intended to be within the scope of the present invention.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, 2H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the invention may exist in both unsolvated and solvated forms. employed when said solvent is water. Examples of solvate forms include, but are not limited to, compounds of the invention in association with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in *Pro-drugs as Novel Delivery Systems, Vol.* 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as pro-moieties' as described, for example, in *Design of Prodrugs* by H. Bundgaard (Elsevier, 1985).

Some examples of prodrugs in accordance with the invention include:

(i) where the compounds of the present invention contain a carboxylic acid functionality (—COOH), a prodrug compound wherein the hydrogen of the carboxylic acid functionality of the compound is replaced by $(C_1$-$C_8)$alkyl to form the corresponding ester;

(ii) where the compounds of the present invention contain an alcohol functionality (—OH), a prodrug compound wherein the hydrogen of the alcohol functionality of the compound is replaced by $(C_1$-$C_6)$ alkanoyloxymethyl to form the corresponding ether; and (iii) where the compounds of the present invention contain a primary or secondary amino functionality (—NH$_2$ or —NHR where R≠ H), a prodrug compound wherein, as the case may be, one or both hydrogens of the amino functionality of the compound I is/are replaced by $(C_1$-$C_{10})$ alkanoyl to form the corresponding amide.

Further examples of replacement groups in accordance with the foregoing examples and examples of other prodrug types may be found in the aforementioned references. Moreover, certain compounds of the present invention may themselves act as prodrugs of other compounds of the present invention.

Also included within the scope of the invention are metabolites of compounds of the present invention, that is, compounds formed in vivo upon administration of the drug. Some examples of metabolites in accordance with the invention include:

(i) where the compounds of the present invention contain a methyl group, a hydroxymethyl derivative thereof (e.g. —CH$_3$->—CH$_2$OH);

(ii) where the compounds of the present invention contain an alkoxy group, a hydroxy derivative thereof (e.g. —OR ->—OH);

(iii) where the compounds of the present invention contain a tertiary amino group, a secondary amino derivative thereof (e.g. —NR$^1$R$^2$->—NHR$^1$ or —NHR$^2$);

(iv) where the compounds of the present invention contain a secondary amino group, a primary derivative thereof (e.g. —NHR$^1$->—NH$_2$);

(v) where the compounds of the present invention contain a phenyl moiety, a phenol derivative thereof (e.g. -Ph->-PhOH); and (vi) where the compounds of the present invention contain an amide group, a carboxylic acid derivative thereof (e.g. —CONH$_2$->COOH).

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

This invention also relates to a method for the treatment of abnormal cell growth in a mammal which comprises administering to said mammal an amount of a compound of the present invention, or a salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In one embodiment of the present invention the anti-tumor agent used in conjunction with a compound of the present invention and pharmaceutical compositions described herein is an anti-angiogenesis agent, kinase inhibitor, pan kinase inhibitor or growth factor inhibitor. Preferred pan kinase inhibitors include Sutent™ (sunitinib), described in U.S. Pat. No. 6,573,293 (Pfizer, Inc, NY, USA). Anti-angiogenesis agents, include but are not limited to the following agents, such as EGF inhibitors, EGFR inhibitors, VEGF inhibitors, VEGFR inhibitors, TIE2 inhibitors, IGF1R inhibitors, COX-II (cyclooxygenase II) inhibitors, MMP-2 (matrix-metalloproteinase 2) inhibitors, and MMP-9 (matrix-metalloproteinase 9) inhibitors.

Preferred VEGF inhibitors, include for example, Avastin (bevacizumab), an anti-VEGF monoclonal antibody of Genentech, Inc. of South San Francisco, Calif. Additional VEGF inhibitors include CP-547,632 (Pfizer Inc., NY, USA), AG13736 (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

VEGF inhibitors useful in the practice of the present invention are described in U.S. Pat. Nos. 6,534,524 and 6,235,764, both of which are incorporated in their entirety for all purposes. Additional VEGF inhibitors are described in, for example in WO 99/24440, in WO 95/21613, WO 99/61422, U.S. Pat. No. 5,834,504, WO 98/50356, U.S. Pat. Nos. 5,883,113, 5,886,020, 5,792,783, 6,653,308, WO 99/10349, WO 97/32856, WO 97/22596, WO 98/54093, WO 98/02438, WO 99/16755, and WO 98/02437, all of which are herein incorporated by reference in their entirety.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

Other antiproliferative agents that may be used in combination with the compounds of the present invention include inhibitors of the enzyme farnesyl protein transferase and inhibitors of the receptor tyrosine kinase PDGFr, including the compounds disclosed and claimed in the following: U.S. Pat. Nos. 6,080,769; 6,194,438; 6,258,824; 6,586447; 6,071,935; 6,495,564; and 6,150,377; 6,596,735; 6,479,513; WO 01/40217; U.S. 2003-0166675. Each of the foregoing patents and patent applications is herein incorporated by reference in their entirety.

PDGRr inhibitors include but are not limited to those disclosed in international patent application publication numbers WO01/40217 and WO2004/020431, the contents of which are incorporated in their entirety for all purposes. Preferred PDGFr inhibitors include Pfizer's CP-673,451 and CP-868,596 and its salts.

Preferred GARF inhibitors include Pfizer's AG-2037 (pelitrexol and its salts). GARF inhibitors useful in the practice of the present invention are disclosed in U.S. Pat. No. 5,608,082 which is incorporated in its entirety for all purposes.

Examples of useful COX-II inhibitors which can be used in conjunction with a compound of Formula (I) and pharmaceutical compositions disclosed herein include CELEBREX™ (celecoxib), parecoxib, deracoxib, ABT-963, MK-663 (etoricoxib), COX-189 (Lumiracoxib), BMS 347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-II inhibitors are disclosed in U.S. Patent Applications US 2005-0148627 and US 2005-0148777, the contents of which are incorporated in their entirety for all purposes.

In a particular embodiment the anti-tumor agent is celecoxib (U.S. Pat. No. 5,466,823), valdecoxib (U.S. Pat. No. 5,633,272), parecoxib (U.S. Pat. No. 5,932,598), deracoxib (U.S. Pat. No. 5,521,207), SD-8381 (U.S. Pat. No. 6,034,256, Example 175), ABT-963 (WO 2002/24719), rofecoxib (CAS No. 162011-90-7), MK-663 (or etoricoxib) as disclosed in WO 1998/03484, COX-189 (Lumiracoxib) as disclosed in WO 1999/11605, BMS-347070 (U.S. Pat. No. 6,180,651), NS-398 (CAS 123653-11-2), RS 57067 (CAS 17932-91-3), 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, or meloxicam.

Other useful inhibitors as anti-tumor agents used in combination with a compound of the present invention and pharmaceutical compositions disclosed herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof.

Preferred COX-I inhibitors include ibuprofen (Motrin), nuprin, naproxen (Aleve), indomethacin (Indocin), nabumetone (Relafen) and combinations thereof.

Targeted agents used in combination with a compound of the present invention and pharmaceutical compositions disclosed herein include EGFr inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Preferred EGFr inhibitors include Iressa, Erbitux, Tarceva and combinations thereof.

Other anti-tumor agents include those selected from pan erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin, TAK-165, CP-724,714, ABX-EGF, HER3 and combinations thereof. Preferred pan erbb receptor inhibitors include GW572016, CI-1033, EKB-569, and Omitarg and combinations thereof.

Additional erbB2 inhibitors include those disclosed in WO 98/02434, WO 99/35146, WO 99/35132, WO 98/02437, WO 97/13760, WO 95/19970, U.S. Pat. Nos. 5,587,458, and 5,877,305, each of which is herein incorporated by reference in its entirety. ErbB2 receptor inhibitors useful in the present invention are also disclosed in U.S. Pat. Nos. 6,465,449, and 6,284,764, and in WO 2001/98277 each of which are herein incorporated by reference in their entirety.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

Further anti-tumor agents may be selected from the following agents, CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131I chTNT 1/b), NBI-3001 (IL-4) and combinations thereof. Additional anti-tumor agents may be selected from the following agents, Canvaxin, GMK vaccine, PEG Interon A, Taxoprexin (DHA/paclitaxel), and combinations thereof.

Other anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438, and combinations thereof.

Additionally, mTOR inhibitors may also be utilized such as CCI-779 (Wyeth) and rapamycin derivatives RAD001 (Novartis) and AP-23573 (Ariad), HDAC inhibitors, SAHA (Merck Inc./Aton Pharmaceuticals) and combinations thereof. Additional anti-tumor agents include aurora 2 inhibitor VX-680 (Vertex), and Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan) imatinib mesylate (Gleevec), and combinations thereof, may be used in combination with a compound of the present invention and pharmaceutical compositions disclosed herein.

The invention also contemplates the use of the compounds of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to the use of the compounds of the present invention together with hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex™ (4'-cyano-3-(4-fluorophenylsulphonyl)-2-hydroxy-2-methyl-3'-(trifluoromethyl)propionanilide, bicalutamide) and combinations thereof.

Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly preferred cytotoxic agents include Camptosar, Erbitux, Iressa, Gleevec, Taxotere and combinations thereof.

The following topoisomerase I inhibitors may be utilized as anti-tumor agents: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics include intercalating antibiotics and include, but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, docetaxel (Taxotere), paclitaxel and combinations thereof.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, topotecan, and combinations thereof.

Preferred cytotoxic topoisomerase inhibiting agents include one or more agents selected from the group consisting of camptothecin, 10-hydroxycamptothecin, 9-aminocamptothecin, irinotecan HCl (Camptosar), edotecarin, epirubicin (Ellence), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, ubenimex and combinations thereof.

Other anticancer agents that can be used in combination with a compound of the present invention include alitretinoin, ampligen, atrasentan bexarotene, bortezomib. Bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoin, and combinations thereof.

Platinum-coordinated compounds include but are not limited to, cisplatin, carboplatin, nedaplatin, oxaliplatin, and combinations thereof.

Camptothecin derivatives include but are not limited to camptothecin, 10-hydroxycamptothecin, 9-aminocamptothecin, irinotecan, SN-38, edotecarin, topotecan and combinations thereof.

Other antitumor agents include mitoxantrone, 1-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682,736; and anti-proliferative agents such as other farnesyl protein transferase inhibitors, for example the farnesyl protein transferase inhibitors. Additionally, specific CTLA4 antibodies that can be used in combination with compounds of the present invention include those disclosed in U.S. Pat. Nos. 6,682,736 and 6,682,736 both of which are herein incorporated by reference in their entirety.

Specific IGF1R antibodies that can be used in the combination methods of the present invention include those disclosed in WO 2002/053596, which is herein incorporated by reference in its entirety.

Specific CD40 antibodies that can be used in the present invention include those disclosed in WO 2003/040170 which is herein incorporated by reference in its entirety.

Gene therapy agents may also be employed as anti-tumor agents such as TNFerade (GeneVec), which express TNFalpha in response to radiotherapy.

In one embodiment of the present invention statins may be used in combination with a compound of the present invention and pharmaceutical compositions thereof. Statins (HMG-COA reducatase inhibitors) may be selected from the group consisting of Atorvastatin (Lipitor™, Pfizer Inc.), Provastatin (Pravachol™, Bristol-Myers Squibb), Lovastatin (Mevacor™, Merck Inc.), Simvastatin (Zocor™, Merck Inc.), Fluvastatin (LeScol™, Novartis), Cerivastatin (Baycol™, Bayer), Rosuvastatin (Crestor™, AstraZeneca), Lovostatin and Niacin (Advicor™, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include Caduet.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In the following examples molecules with a single chiral center, unless otherwise noted or indicated by the structural formula or chemical name, exist as a racemic mixture. Those molecules with two or more chiral centers, unless otherwise noted or indicated by the structural formula or chemical name, exist as a racemic mixture of diastereomers. Single enantiomers/diastereomers may be obtained by methods known to those skilled in the art.

$^1$H-NMR spectra were recorded on a Bruker instrument operating either at 300 MHz, or 400 MHz and $^{13}$C-NMR spectra were recorded operating at 75 MHz.

The following abbreviations may be used herein: Et$_2$O (diethyl ether); DMF (N,N-dimethylformamide); THF (tetrahydrofuran); DCM (dichloro-methane); DMA (dimethyl acetal); DBU (1,8-diazabicyclo[5.4.0]undec-7-ene); LiHMDS or LHMDS (lithium hexamethyldisilazide); TBME (tert-butyl methyl ether); LDA (lithium diisopropylamide); DMSO or dmso (dimethylsulfoxide); MeOH (methanol); EtOH (ethanol); BuOH (butanol); EtOAc (ethyl acetate); THF (tetrahydrofuran); Ac (acetyl); Me (methyl); Et (ethyl); Ph (phenyl); TMSI (trimethylsilyliodide); DSC(N,N'-disuccinimidyl carbonate); CDI (1,1'-carbonyldiimidazole); Boc (tert-butoxycarbonyl); nBuLi (n-butyl lithium); EDC (1-(3-dimethylaminopropyl)-3-ethylcarbodiimide hydrochloride); HOBt (N-hydroxybenzitriazole hydrate); DME (1,2-dimethoxyethane); Pd(dba)$_2$ (bis(dibenzylideneacetone)palladium(0)); and RT or rt (room temperature).

Example 1

2-amino-N-bicyclo[1.1.1]pent-1-yl-4-{2,4-dichloro-6-[2-(4-chloro-1H-pyrazol-1-yl)ethoxy]phenyl}-5,7-dihydro-6H-pyrrolo[3,4-d]pyrimidine-6-carboxamide A solution of compound 1b (in 3 mL of DMF) and TEA (1 mL, 7 mmol) were added to a solution of compound 1a (51 mg, 0.11 mmol) in DMF (2 mL). The mixture was heated at 70° C. for 3 h. The reaction was cooled to room temperature. Water (20 mL) was added to the reaction mixture and EtOAc (2×50 mL) was added to extract the aqueous solution. The combined organic layer was dried, filtered, and concentrated to get a brown yellow oil. Isolation by preparative HPLC gave compound 1 (23 mg, 0.043 mmol) as a white solid in 39% yield. $^1$H NMR (400 MHz, DMSO-d$_6$) δ ppm 1.94 (s, 6 H), 2.35 (s, 1 H), 3.72 (d, J=13.14 Hz, 1 H), 3.96 (d, J=13.14 Hz, 1 H), 4.27-4.33 (m, 2 H), 4.33-4.48 (m, 4 H), 6.78 (s, 2 H), 6.90 (s, 1 H), 7.28 (d, J=1.77 Hz, 1 H), 7.35 (d, J=1.52 Hz, 1 H), 7.36 (s, 1 H), 7.49 (s, 1 H). LCMS (M+H)$^+$ 535.

Anal. Calcd for C$_{23}$H$_{22}$Cl$_3$N$_7$O$_2$.1 H$_2$O: C, 49.97; H, 4.38; N, 17.73. Found: C, 50.36; H, 4.23; N, 17.40.

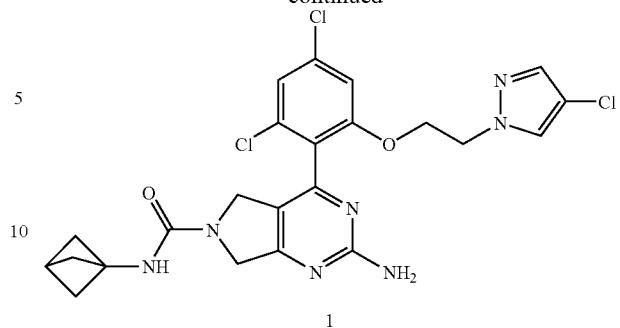

Compound 1a

4-{2,4-dichloro-6-[2-(4-chloro-pyrazol-1-yl)-ethoxy]-phenyl}-6,7-dihydro-5H-pyrrolo[3,4-d]pyrimidin-2-ylamine Hydrogen chloride (0.5 mL, 2 mmol, 4M in dioxane) was added to a solution of compound 1c (55.7 mg, 0.11 mmol) in dichloromethane (10 mL). The mixture was stirred at room temperature for 12 h and monitored by LC/MS. The solvent was evaporated to afford compound 1a as a light yellow solid. This crude residue was used for the synthesis of compound 1 without further purification.

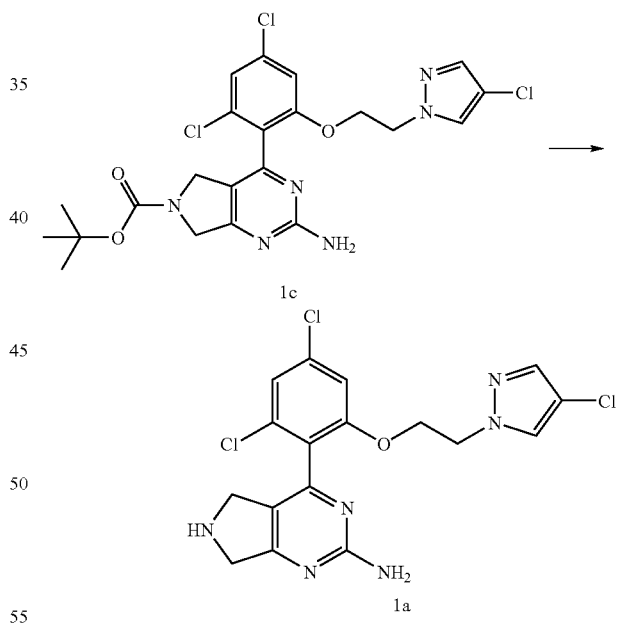

Compound 1b

Imidazole-1-carboxylic acid bicyclo[1.1.1]pent-1-ylamide

Triethylamine (0.1 mL, 0.5 mmol) was added to a solution of bicyclo[1.1.1]-pentan-1-amine hydrogen chloride (19 mg, 0.16 mmol) and 1,1'-carbonyldiimidazole (32 mg, 0.192 mmol) in DMF (2 mL) (clear solution turned into suspen-

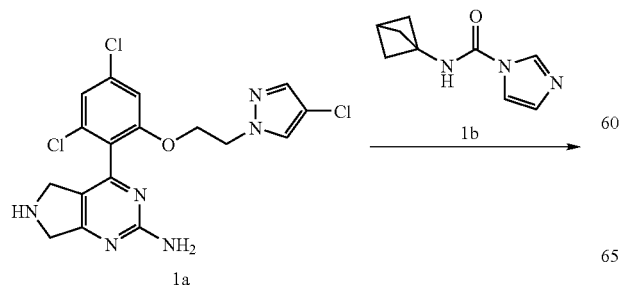

sion). The suspension was used for the synthesis of compound 1 without further isolation of compound 1b.

Compound 1c 2-amino-4-{2,4-dichloro-6-[2-(4-chloro-pyrazol-1-yl)-ethoxy]-phenyl}-5,7-dihydro-pyrrolo[3,4-d]pyrimidine-6-carboxylic acid tert-butyl ester Potassium carbonate (100 mg, 0.7 mmol) and compound 1e (120 mg, 0.5 mmol) were added sequentially to a solution of compound 1d (98 mg, 0.25 mmol) in DMF (2 mL). The mixture was microwaved at 120° C. for 40 min. Water (10 mL) and EtOAc (50 mL) were added to the reaction mixture to stir. The organic layer was collected, dried, filtered, and concentrated to get a yellowish oil. This oil residue was purified by silica gel chromatography (gradient elution 50→60% EtOAc in hexane) to give compound 1c (62.7 mg, 48.3% yield) as an oil. This oil was lyophilized to a white solid. $^1$H NMR (400 MHz, DMSO-d$_6$) δ ppm 1.38-1.48 (m, 9 H), 3.63 (t, J=13.89 Hz, 1 H), 3.91 (dd, J=24.00, 13.39 Hz, 1 H), 4.28-4.34 (m, 2 H), 4.40 (d, J=3.54 Hz, 4 H), 6.81 (br. s., 2 H), 7.27 (s, 1 H), 7.32-7.34 (m, 1 H), 7.39 (s, 1 H), 7.55 (s, 1 H). LCMS (M+H)$^+$ 527.

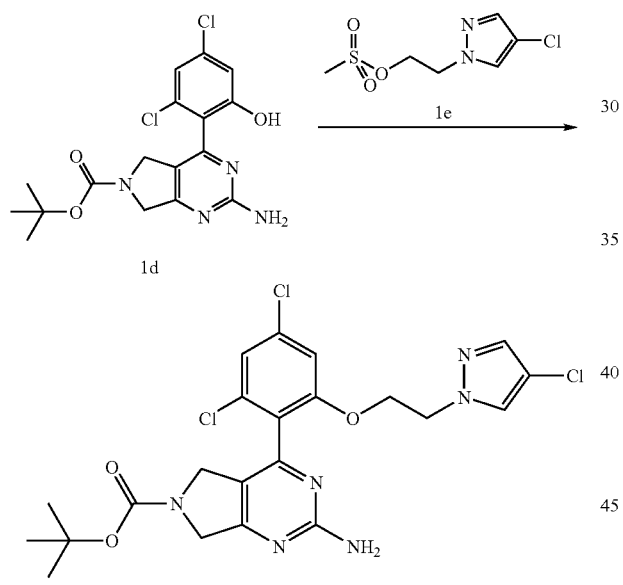

Compound 1d 2-amino-4-(2,4-dichloro-6-hydroxy-phenyl)-5,7-dihydro-pyrrolo[3,4-d]pyrimidine-6-carboxylic acid tert-butyl ester Sodium carbonate (1.2 g, 11 mmol) in 5.6 mL of H$_2$O was added to a mixture of compound 1g (770 mg, 3.7 mmol) and compound 1f (1000 mg, 2.7 mmol) in 1,4-dioxane (45 mL). The mixture was purged with nitrogen several times and then tetrakis (triphenylphsophine) palladium (0) (270 mg) was added. The reaction mixture and the resulting solution was heated to 80° C. for 12 h. Water (50 mL) was added to the reaction mixture to quench the reaction. EtOAc (2×100 mL) was then added to extract the aqueous solution. The combined organic layer was dried, filtered, and concentrated to get a brown oil. This oil residue was purified by silica gel chromatography (gradient elution 30→40% EtOAc in hexane) to give compound 1d (590 mg, 40% yield) as light brown foam. This oil was lyophilized to a white solid. $^1$H NMR (400 MHz, DMSO-d$_6$) δ ppm 1.37-1.47 (m, J=12.88 Hz, 9 H), 4.07-4.24 (m, 2 H), 4.42 (d, J=7.58 Hz, 2 H), 6.82 (s, 2 H), 6.95 (d, J=1.77 Hz, 1 H), 7.08-7.21 (m, 1 H), 10.67 (s, 1 H). LCMS (M+H)$^+$ 398. Anal. Calcd for C$_{17}$H$_{18}$Cl$_2$N$_4$O$_3$.0.5 CH$_2$Cl$_2$: C, 49.80; H, 4.36; N, 12.74. Found: C, 47.41; H, 4.46; N, 12.71.

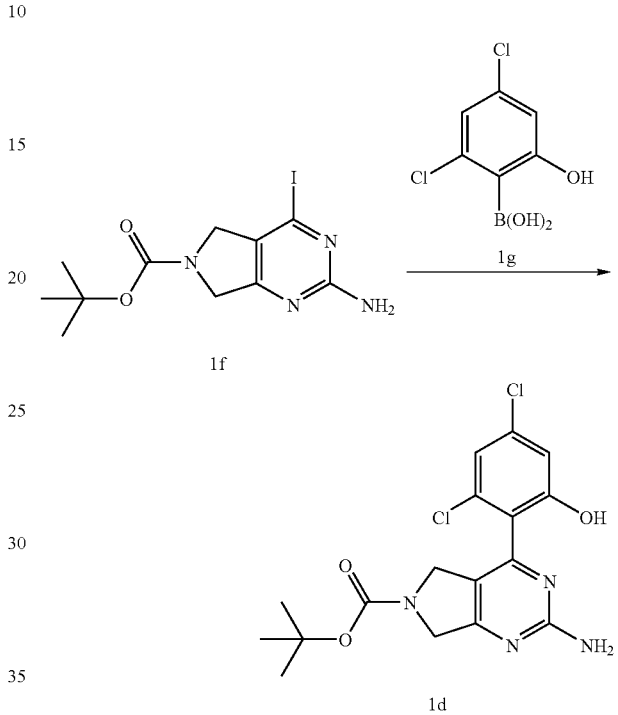

Compound 1e

Methanesulfonic acid 2-(4-chloro-pyrazol-1-yl)-ethyl ester

Sodium hydride (136 mg, 3.4 mmol, 60% dispersion in mineral oil) was added to a solution of 4-chloropyrazole (342 mg, 3.3 mmol) in DMF (10 mL) under N$_2$. The mixture was stirred at room temperature for 1 h. The reaction was transferred to methanesulfonic acid 2-bromo-ethyl ester (820 mg, 4 mmol, synthesized by following literature procedure, J. Med. Chem. 1983, 26(8), p1168) via a syringe. The mixture was stirred at 70° C. for 3 h. Water (30 mL) was added to the mixture and EtOAc (2×100 mL) was added to extract the aqueous solution. The combined organic layer was dried, filtered, and concentrated to get a brown oil. This oil residue was purified by silica gel chromatography (gradient elution 20→30% EtOAc in hexane) to give compound 1e (59 mg, 8% yield) as a brown oil. $^1$H NMR (400 MHz, CDCl$_3$-d) δ ppm 2.89 (s, 3 H), 4.38-4.43 (m, 2 H), 4.55-4.61 (m, 2 H), 7.49 (s, 1 H), 7.49 (s, 1 H).

Compound 1f 2-amino-4-iodo-5,7-dihydro-pyrrolo[3,4-d]pyrimidine-6-carboxylic acid tert-butyl ester To a suspension of ethyl 2-amino-4-chloro-5,7-dihydro-6H-pyrrolo[3,4-d]pyrimidine-6-carboxylate (compound I(C)

when PG¹ is EtOC(O)— and X is Cl), (30.6 g, 126 mmol, 1.0 eq) in 750 mL acetonitrile was added iodotrimethylsilane (100 mL, 703 mmol, 5.6 eq), and the resulting reaction mixture was heated at reflux for 4 h. After cooling down to ambient temperature, the reaction mixture was quenched with MeOH (27 mL), and concentrated to dryness in vacuo. Traces of MeOH were removed via coevaporation with toluene (150 mL). The resulting residue was treated with Et₂O (200 mL), and the precipitates were filtered and washed with Et₂O. The crude brown powder was then stirred in refluxing EtOAc (250 mL), cooled to ambient temperature and the solid was collected by filtration and washed with ethyl acetate to afford the desired product as a brown powder (52.2 g, ~79%). This material was used for the next step reaction without further purification. ¹H NMR (300 MHz, DMSO-D6) δ ppm 9.47 (br s, 2H), 4.37 (s, 2H), 4.25 (s, 2H). LCMS (M+H)⁺: 263.2.

The above brown powder (52.2 g, ~100 mmol) was dissolved in dioxane (150 mL) and water (150 mL). In addition, diisopropylethylamine (69.7 mL, 400 mmol) and Boc2O (43.6 g, 200 mmol) were added and the mixture warmed to 45° C. The mixture was stirred at ambient temperature and followed by NMR for an additional 1.5 h. The product was poured into EtOAc (3.0 L) and saturated NaHCO₃ (aq.) (1.0 L), the layers were separated and the aqueous layer was washed once more with EtOAc (1.0 L). The combined organic layers were dried (Na₂SO₄), filtered and concentrated in vacuo. The product was filtered over silica using EtOAc (3 L) as an eluent, product not completely pure. Filtration over a plug of silica using EtOAc (2 L) gave compound 1f (8 g, 22%) as a tan solid. ¹H NMR (400 MHz, DMSO-D6) δ ppm 1.44 (d, J=4.80 Hz, 9 H), 4.25 (d, J=13.14 Hz, 2 H), 4.42 (d, J=8.34 Hz, 2 H), 7.06 (s, 2 H). LCMS (M+H)⁺: 348.2.

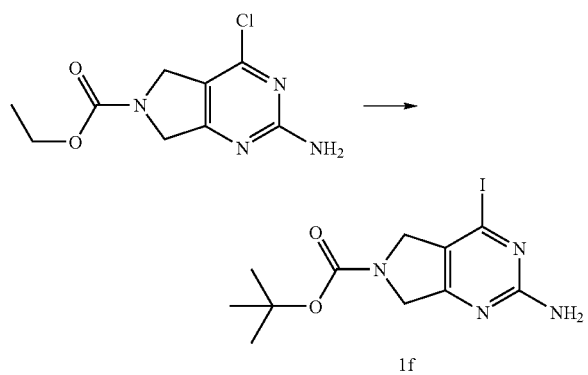

I(C), where PG¹ is EtOC(O)—, X is Cl

Preparation of Compound I(C)

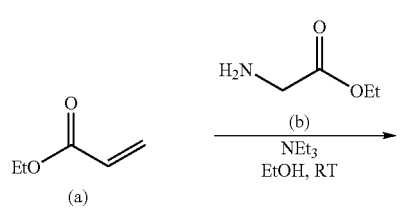

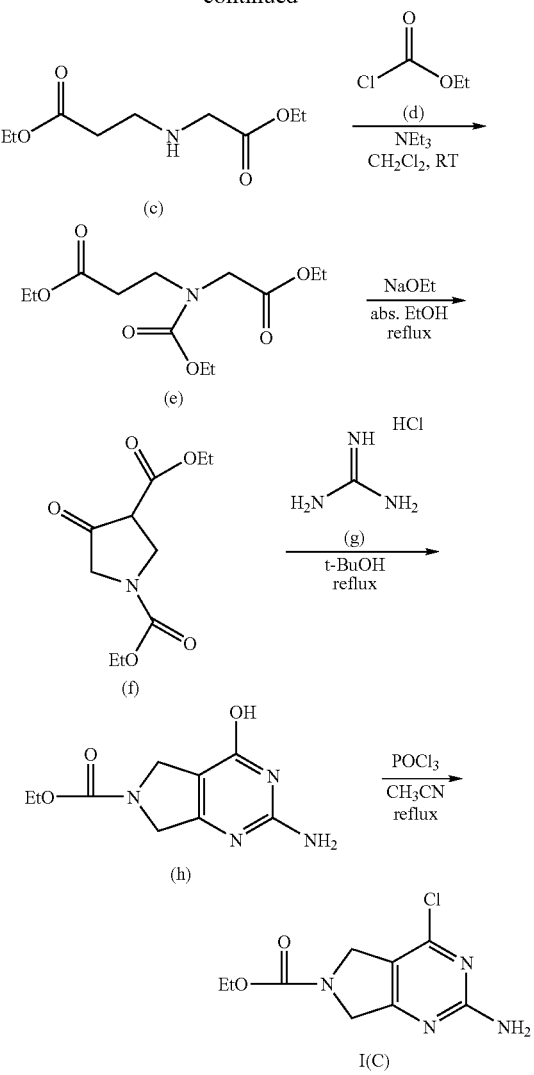

Step 1. ethyl N-(ethoxycarbonyl)-β-alaninate (c)

Ethyl acrylate (a) (50 mL, 460 mmol, 1.1 eq), glycine ethyl ester hydrochloride (b) (58.4 g, 418 mmol, 1 eq), and triethylamine (58.3 mL, 418 mmol, 1 eq) in absolute EtOH (960 mL) was stirred at ambient temperature for approximately 72 h. After reaction was complete, volatile components were removed under vacuum and the crude intermediate (c) was carried on directly.

Step 2. ethyl N-(ethoxycarbonyl)-N-(2-ethoxy-2-oxoethyl)-β-alaninate (e)

Crude intermediate (c) (418 mmol) was dissolved in CH₂Cl₂ (275 mL) and triethylamine (58.3 mL, 418 mmol) was added followed by ethyl chloroformate (d) (39.8 mL, 418 mmol). The reaction was stirred at ambient temperature for about 24 h. After the reaction was complete, the volatile components were removed under vacuum. The crude product was then distilled under vacuum (about 5 mm Hg) and dissolved in EtOAc which was washed with aqueous saturated KHSO₄×3, with brine×1 and dried over Na₂SO₄. Following filtration, the volatile components were removed under vacuum to afford intermediate (e) as a clear oil (74.8 g, 272 mmol) in 65% yield over two steps.

Step 3. diethyl 4-oxopyrrolidine-1,3-dicarboxylate (f)

Intermediate (e) (18.0 g, 65.2 mmol) was added to an ice bath cooled solution of NaOEt (32.6 mL) (21% by weight in EtOH) in absolute EtOH (41.7 mL) under a nitrogen atmosphere. The ice bath was removed and the mixture was heated at 80° C. for about 12 h until the condensation was complete as observed by TLC. The mixture was poured onto ice/water and extracted into EtOAc. The solvent was dried with $Na_2SO_4$, filtered, and evaporated to afford crude intermediate (f) as an off white solid (14.05 g) which was carried on without purification.

Step 4. ethyl 2-amino-4-hydroxy-5,7-dihydro-6H-pyrrolo[3,4-d]pyrimidine-6-carboxylate (h)

A suspension of intermediate (f) (14.05 g) and guanidine carbonate (g) (16.6 g, 91.9 mmol) was refluxed in t-butanol (147 mL) for about 6 h. The mixture was allowed to cool to ambient temperature for about 2 h. The volatile components were removed under vacuum and water was added. The pH was adjusted to about 6-7 using $KHSO_4$. The resulting slurry was filtered to collect the solids which were washed with water followed by EtOAc. The solids were dried under vacuum to afford intermediate (h) as cream solids (11.9 g, 53.1 mmol) in 87% yield. $^1$H NMR (400 MHz, DMSO-D6) δ ppm 11.01 (s, 1H), 6.97 (s, 0.5H, possible tautomer), 6.70 (s, 2H), 4.25 (s, 4H), 4.13-4.03 (m, 2H), 1.22 (t, 3H). LCMS (M+H)$^+$: 225.2.

Step 5. ethyl 2-amino-4-chloro-5,7-dihydro-6H-pyrrolo[3,4-d]pyrimidine-6-carboxylate I(C)

Intermediate (h) (11 g, 49 mmol) was azeotroped×2 with toluene. Anhydrous acetonitrile (250 mL) and $POCl_3$ (25 mL, 270 mmol) were added and the mixture was refluxed for about 2.5 h. Additional $POCl_3$ (50 mL) was added and the mixture was refluxed for an additional 2 h. The volatile components were concentrated under vacuum at 40° C. to give a red solution. A minimum amount of dry acetonitrile was added until the solution was readily transferable whereupon it was poured onto ice in a large beaker. The flask was further rinsed with a small amount of acetonitrile which was added to the ice. Water (about 50 mL) was added to the ice mixture to help it with stirring. Concentrated $NH_4OH$ (25 mL) was added slowly with stirring until the ice slurry mixture was strongly basic, then 50% aqueous NaOH (25 mL) was also added to the still stirring slurry of ice. Additional ice was added. After about 5 minutes stirring as ice slurry, EtOAc was added. After stirring in the beaker for several more minutes, water was added to help melt the ice. The mixture was poured into a separatory funnel and the layers were allowed to partition. The aqueous layer was extracted with EtOAc×3. The combined EtOAc extracts were washed ×2 with saturated aqueous $KHSO_4$, ×2 with saturated aqueous $NaHCO_3$, ×1 with brine, dried over $Na_2SO_4$, filtered and evaporated to afford a pale pink powder which was triturated with ethyl acetate to give compound I(C) as pale pink solids (6.8 g, 28 mmol) in 57% yield. HPLC/LCMS purity was greater than 90%. $^1$H NMR (400 MHz, DMSO-D6) δ ppm 7.20 (s, 2H), 4.48 (s, 2H), 4.45 (s, 2H), 4.17-4.08 (m, 2H), 1.24 (t, 3H). LCMS (M+H)$^+$: 243.2, 245.2.

Preparation of Compound 1g 2,4-dichloro-6-hydroxyphenylboronic acid

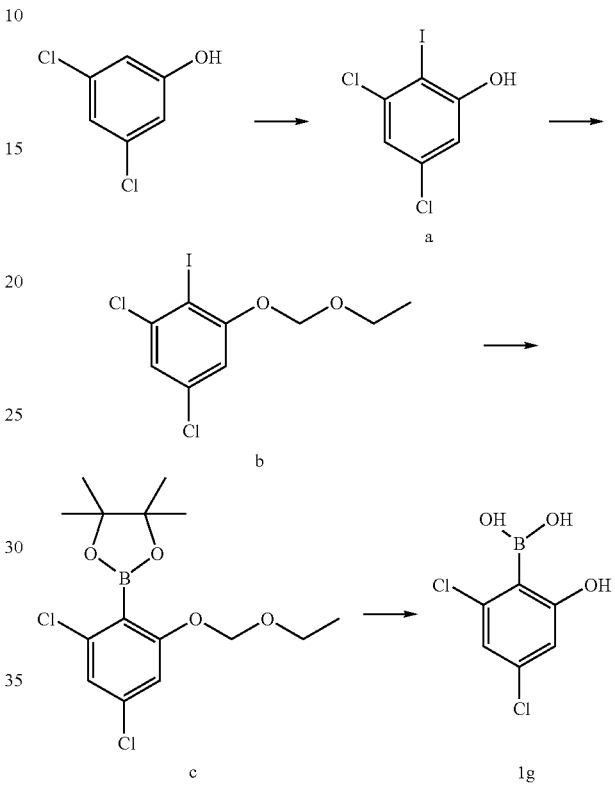

Preparation of Compound a:

To a solution of 3,5-dichloro-phenol (70 g, 0.43 mol) in dry toluene (1 L) was added NaH (51.5 g, 1.29 mol) portionwise at 0° C. under $N_2$ atmosphere. After the addition, the resulting mixture was allowed to warm up to room temperature and stirred for 20 minutes. The suspension was then cooled back to 0° C., and iodine (253.81 g, 91.5 mol) was added slowly. Then the reaction mixture was stirred at room temperature overnight. TLC (petroleum ether/$CH_2Cl_2$ 1:1) indicated complete consumption of starting material. The reaction mixture was quenched with 1 N HCl (1 L) and diluted with ether (1 L). The separated organic layer was washed with brine (500 mL), dried over $Na_2SO_4$ and concentrated in vacuo to give crude compound 2, which was purified by column chromatography (silica gel, petroleum ether/$CH_2Cl_2$ from 5:1 to 1:1) to yield pure compound a (85 g, yield: 68%) as a white solid.

Preparation of Compound b:

A mixture of compound a (67 g, 0.23 mol), chloromethoxy-ethane (31.8 g, 0.29 mol) and $Cs_2CO_3$ (63.7 g, 0.2 mol) in DMF (600 mL) was stirred at room temperature for 2 hours. TLC (petroleum ether/EtOAc 2:1) indicated complete consumption of compound a. The reaction mixture was washed with $H_2O$ (500 mL×3) and brine (500 mL), dried over $Na_2SO_4$ and concentrated in vacuo to give crude compound 3, which was purified via column chromatography (silica gel, EtOAc/hexane 1:50) to yield pure compound b (80 g, 100%) as a yellow solid.

Preparation of Compound c:

A solution of compound b (77 g, 0.22 mol), 4,4,5,5-tetramethyl-[1,3,2]dioxaborolane (57 g, 0.44 mol) and Et₃N (92 mL, 0.66 mol) in dioxane (500 mL) was purged with N₂ for 30 minutes. Then Pd(OAc)₂ (2.7 g, 0.011 mol) and biphenyl-2-yl-dicyclohexyl-phosphane (8.5 g, 0.022 mol) were added to the resulting mixture. After the addition, the reaction mixture was stirred at 80° C. for 1.5 hours. TLC (petroleum ether/EtOAc 30:1) indicated complete consumption of compound b. The resulting mixture was washed with saturated NH₄Cl (500 mL), H₂O (500 mL) and brine (500 mL) in sequence, dried over Na₂SO₄ and concentrated in vacuo to give crude compound c, which was purified by column chromatography (silica gel, petroleum ether/EtOAc from 5:1 to 1:1) to yield pure compound c (35 g, yield: 45%) as a brown solid.

Preparation of compound 1g:

To a stirred solution of compound c (35 g, 0.1 mol) in dry CH₂Cl₂ (200 mL) was added BBr₃ (125 g, 0.5 mol) dropwise at 0° C. under N₂ atmosphere. After stirring for 20 minutes, the reaction mixture was poured into ice water, basified to pH ~10 by 3 N NaOH (100 mL) and the organic layer was separated. The separated aqueous layer was adjusted to pH ~3 with 1 N HCl (500 mL) and extracted with EtOAc (500 mL×3), the combined organic layers were washed with brine (1.0 L), dried over Na₂SO₄ and concentrated in vacuo to yield compound 1g (39.7 g, yield: 80%) as a white solid. ¹H NMR (400 MHz, MeOD): δ 6.875-6.878 (d, 1H), 6.727-6.737 (d, 1H).

Example 2

2-amino-N-cyclopropyl-4-{2,4-dichloro-6-[2-(4-chloro-1H-pyrazol-1-yl)ethoxy]phenyl}-5,7-dihydro-6H-pyrrolo[3,4-d]pyrimidine-6-carboxamide Potassium carbonate (46 mg, 0.33 mmol) and compound 2b and 2c (82 mg, 0.5 mmol) were added sequentially to a solution of compound 2a (42 mg, 0.11 mmol) in DMF (3 mL). The mixture was heated at 120° C. for 40 min in a microwave. Water (10 mL) and EtOAc (50 mL) were added to the reaction mixture and stirred. The organic layer was collected, dried, filtered, and concentrated to get a yellowish oil. This oil residue was purified by preparative HPLC to give compound 2 (31.5 mg, 56% yield) as a white solid. ¹H NMR (400 MHz, DMSO-d₆) δ ppm 0.35-0.45 (m, 2 H), 1.84 (s, 1 H), 3.69 (d, J=13.39 Hz, 1 H), 3.95 (dd, J=13.01, 1.39 Hz, 1 H), 4.13-4.47 (m, 6 H), 6.36 (s, 1 H), 6.77 (s, 2 H), 7.27 (d, J=1.77 Hz, 1 H), 7.33 (d, J=1.77 Hz, 1 H), 7.35 (s, 1 H), 7.48 (s, 1 H). LCMS (M+H)⁺ 510.

Anal. Calcd for C₂₁H₂₀Cl₃N₇O₂.1.25H₂O: C, 47.47; H, 4.27; N, 18.45. Found: C, 47.13; H, 4.01; N, 18.72.

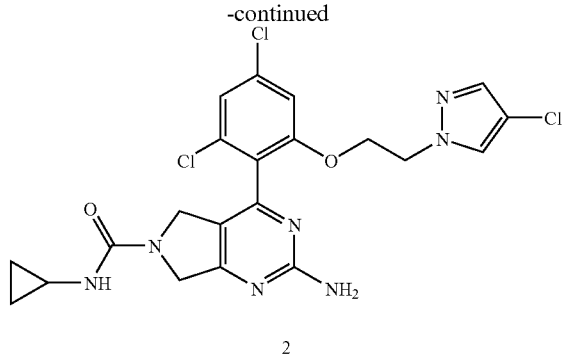

Compound 2a 2-amino-4-(2,4-dichloro-6-hydroxy-phenyl)-5,7-dihydro-pyrrolo[3,4-d]pyrimidine-6-carboxylic acid cyclopropylamide Sodium carbonate solution (7.8 mL, 2M, 9.2 mmol) were added to a solution of compound 1g (668 g, 3.2 mmol) and compound III(B)-1 (1.1 g, 3.1 mmol) in 1,4-dioxane (30 mL). The mixture was purged with N2 for 15 min, then tetrakis (triphenylphsophino) palladium (0) (355 mg, 0.3 mmol) was added. The resulting mixture was stirred at 80° C. for 12 h. The reaction mixture was filtered through Celite pad and washed well with MeOH. The filtrate was concentrated by vacuum. The residue was partitioned between EtOAc (2×500 mL) and brine (100 mL). The organic layer was dried, filtered, and concentrated to get a yellow oil. This yellow oil was treated with CH₂Cl₂ and hexane and the precipatate was collected and washed well with hexane to give compound 2a (1.1 g, 97%). 1H NMR (400 MHz, DMSO-d₆) δ ppm 0.33-0.44 (m, 2 H), 0.46-0.59 (m, 2 H), 0.80-0.91 (m, 1 H), 4.11 (br. s., 2 H), 4.39 (s, 2 H), 6.45 (d, J=2.78 Hz, 1 H), 6.74-6.84 (m, 2 H), 6.91-7.00 (m, 1 H), 7.14 (d, J=1.77 Hz, 1 H), 10.64 (br. s., 1 H). LCMS (M+H)⁺: 380.

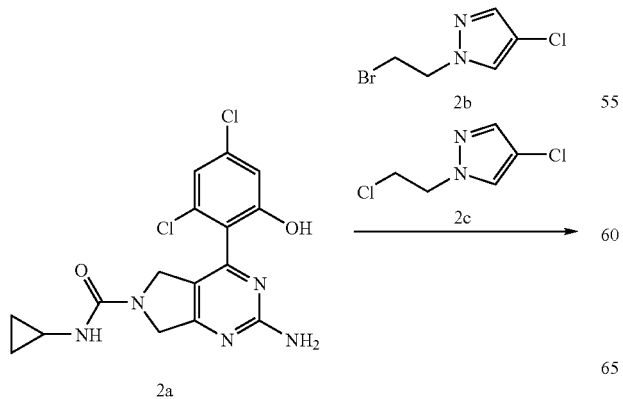

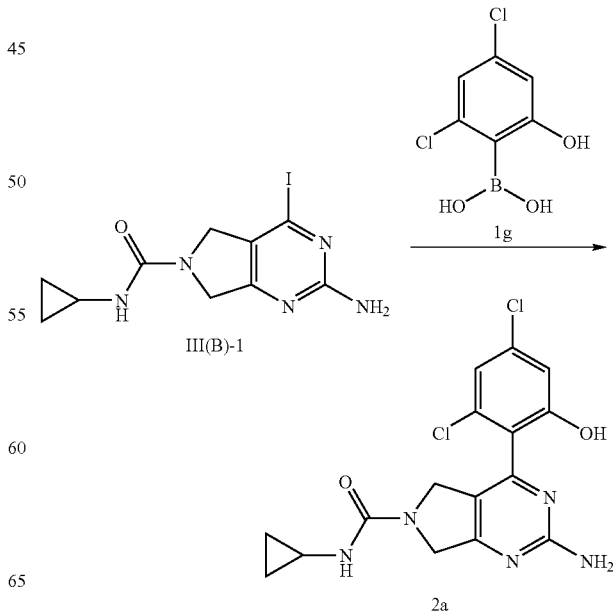

Compound III(B)-1

2-amino-4-iodo-5,7-dihydro-pyrrolo[3,4-d]pyrimidine-6-carboxylic acid cyclopropylamide Iodotirmethylsilane (25 mL, 176 mmol) was added to a suspension of compound I(C) (8.36 g, 24.7 mmol) in ACN (200 mL) at room temperature. The mixture was refluxed at 90° C. for 3 h. The reaction mixture was cooled to rt, and then quenched with MeOH (10 mL), concentrated by vacuum. The residue was treated with Et2O (100 mL), and the precipitate was collected by filtration and washed well with ether to give the HI salt of 4-Iodo-6,7-dihydro-5H-pyrrolo[3,4-d]pyrimidin-2-ylamine as a brown color solid (14.4 g, 81%). This crude product was ready to use for next reaction without further purification.

1H NMR (400 MHz, DMSO-$d_6$) δ ppm 4.25 (t, J=4.80 Hz, 1 H), 4.29-4.47 (m, 3 H), 6.02 (br. s., 2 H), 9.42 (br. s., 1 H). LCMS (M+H)$^+$: 263.

A solution of compound 10a (in 5 mL of DMF) and TEA (2.8 mL, 20 mmol) were added to a solution of 4-Iodo-6,7-dihydro-5H-pyrrolo[3,4-d]pyrimidin-2-ylamine HI salt (2590 mg, 5 mmol) in DMF (10 mL). The mixture was heated at 65° C. for 2 h. The reaction was cooled down to room temperature. Water (50 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→10% $CH_3OH$ in dichloromethane) to give compound III(B)-1 as a pale yellow solid (1.1 g, 62% yield). $^1$H NMR (400 MHz, DMSO-d6) δ ppm 0.38-0.48 (m, 2 H), 0.51-0.64 (m, 2 H), 2.53-2.59 (m, 1 H), 4.24 (s, 2 H), 4.36-4.44 (m, 2 H), 6.56 (d, J=2.78 Hz, 1 H), 6.96-7.10 (m, 2 H). LCMS (M+H)$^+$: 346.0.

Preparation of Compounds 2b and 2c

4-chloro-1-(2-bromo-ethyl)-1H-pyrazole and 4-Chloro-1-(2-chloro-ethyl)-1H-pyrazole Sodium hydride (293 mg, 7.3 mmol, 60% dispersion in mineral oil was added to a solution of chloropyrazole (500 mg, 4.9 mmol) in DMF (8 mL) at room temperature. The mixture was stirred at room temperature for 40 min. The mixture was then canulated to a 1-bromo-2-chloroethane (856 mg, 5.9 mmol, in 1 mL of DMF). The mixture was heated to 60° C. for 12 h. Water (20 mL) was added to the reaction mixture and EtOAc (2×50 mL) was added to extract the aqueous solution. The combined organic layer was dried, filtered, and concentrated to get a waxy oil residue. LC/MS and $^1$H-NMR indicated it's the mixture of two products, compound 2b and compound 2c (498 mg, 61.9% yield).

Example 3

2-amino-N-bicyclo[1.1.1]pent-1-yl-4-{2,4-dichloro-6-[2-(4-chloro-1H-pyrazol-1-yl)ethoxy]phenyl}-5,7-dihydro-6H-pyrrolo[3,4-d]pyrimidine-6-carboxamide A solution of compound 1b (in 3 mL of DMF) and TEA (1 mL, 7 mmol) were added to a solution of compound 3a (50 mg, 0.11 mmol) in DMF (2 mL). The mixture was heated at 70° C. for 3 h. The reaction was cooled down to room temperature. Water (20 mL) was added to the reaction mixture and EtOAc (2×50 mL) was added to extract the aqueous solution. The combined organic layer was dried, filtered, and concentrated to get a brown yellow oil. Isolation by preparative HPLC gave compound 2 (34 mg, 0.072 mmol) as a white solid in 63% yield. 1H NMR (400 MHz, dmso-$d_6$) δ ppm 1.89-1.97 (m, 6 H), 1.99 (s, 3 H), 2.26-2.39 (m, 1 H), 3.49 (d, J=12.38 Hz, 1 H), 3.82 (dd, J=12.76, 1.89 Hz, 1 H), 4.19-4.46 (m, 6 H), 6.01 (t, J=2.02 Hz, 1 H), 6.67 (s, 2 H), 6.82 (s, 1 H), 6.99 (s, 1 H), 7.02 (d, J=1.52 Hz, 1 H), 7.19 (d, J=2.02 Hz, 1 H), 7.30 (d, J=1.26 Hz, 1 H). LCMS (M+H)$^+$ 481.

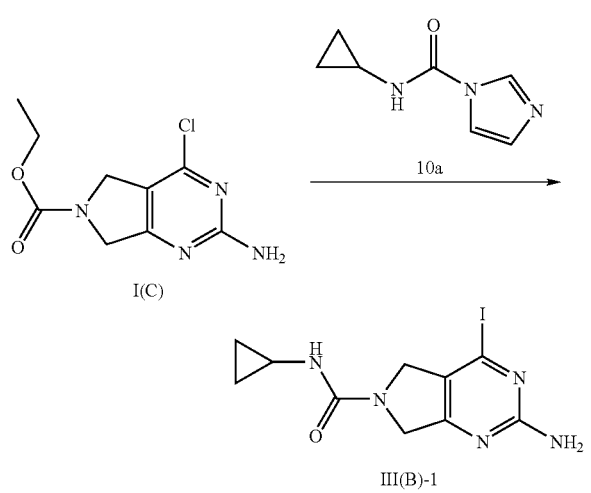

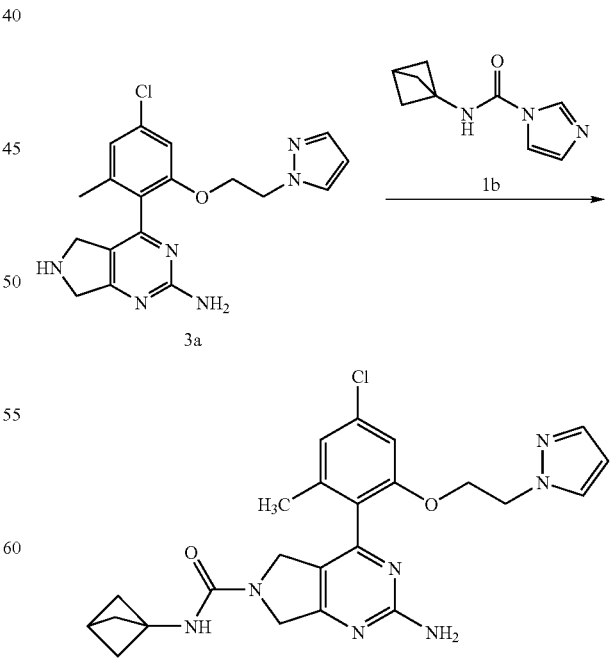

Compound 3a

4-[4-chloro-2-methyl-6-(2-pyrazol-1-yl-ethoxy)-phenyl]-6,7-dihydro-5H-pyrrolo[3,4-d]pyrimidin-2-ylamine (110646-545)

Hydrogen chloride (0.5 mL, 2 mmol, 4M in dioxane) was added to a solution of compound 3b (58 mg, 0.12 mmol) in dichloromethane (10 mL). The mixture was stirred at room temperature for 12 h and monitored by LC/MS. The solvent was evaporated to afford compound 3a as a light yellow solid residue. This crude residue was used for the synthesis of compound 1 without further purification.

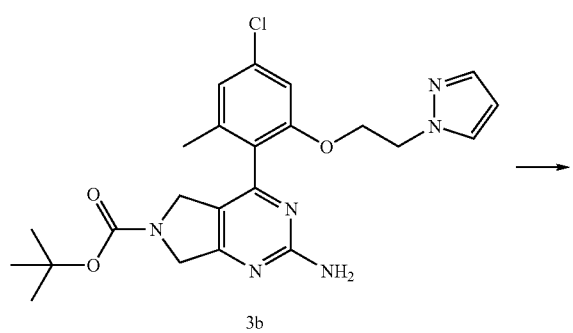

3b

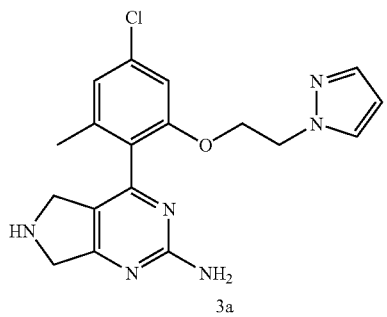

3a

Compound 3b 2-amino-4-[2,4-dichloro-6-(2-pyrazol-1-yl-ethoxy)-phenyl]-5,7-dihydro-pyrrolo[3,4-d]pyrimidine-6-carboxylic acid tert-butyl ester Potassium carbonate (100 mg, 0.7 mmol) and 1-(2-Bromo-ethyl)-1H-pyrazole (synthesized followed the literature procedure: Org. Letters, 2006, 8(10), p. 2043) (67 mg, 0.38 mmol) were added sequentially to a solution of compound 3c (96 mg, 0.26 mmol) in DMF (2 mL). The mixture was microwaved at 120° C. for 40 min. Water (10 mL) and EtOAc (50 mL) were added to the reaction mixture to stir. The organic layer was collected, dried, filtered, and concentrated to get a yellowish oil. This oil residue was purified by silica gel chromatography (gradient elution 100% EtOAc) to give compound 3b (69.3 mg, 58% yield) as an oil. This oil was lyophilized to a white solid. $^1$H NMR (400 MHz, dmso-$d_6$) δ ppm 1.46 (s, 9 H), 1.99 (s, 3 H), 3.39-3.59 (m, 1 H), 3.77 (d, J=22.48 Hz, 1 H), 4.20-4.28 (m, 1 H), 4.29-4.34 (m, 3 H), 4.34-4.45 (m, 2 H), 6.03 (q, J=2.02 Hz, 1 H), 6.70 (s, 2 H), 6.98 (s, 1 H), 7.03 (s, 1 H), 7.24 (dd, J=4.80, 2.02 Hz, 1 H), 7.31 (dd, J=15.92, 1.52 Hz, 1 H). LCMS (M+H)$^+$ 472.

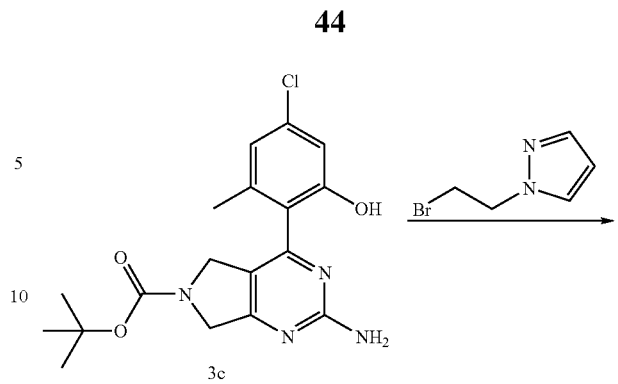

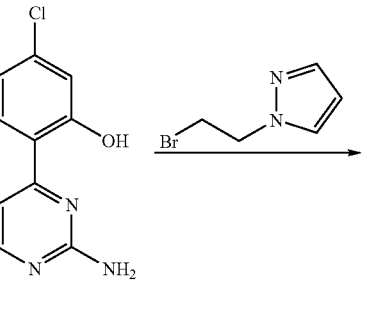

3b

Compound 3c 2-amino-4-(2,4-dichloro-6-hydroxy-phenyl)-5,7-dihydro-pyrrolo[3,4-d]pyrimidine-6-carboxylic acid tert-butyl ester Sodium carbonate (512 mg, 4.8 mmol) in 2.4 mL of H$_2$O was added to a mixture of compound 3d (300 mg, 1.6 mmol) and compound 1f (583 mg, 1.6 mmol) in 1,4-dioxane (10 mL). The mixture was purged with nitrogen several times and then tetrakis (triphenylphosphino) palladium (0) (116 mg) was added. The reaction mixture and the resulting solution was heated at 120° C. for 40 min in microwave. Water (50 mL) was added to the reaction mixture to quench the reaction. EtOAc (2×100 mL) was then added to extract the aqueous solution. The combined organic layer was dried, filtered, and concentrated to get a brown oil. This oil residue was purified by silica gel chromatography (gradient elution 60→70% EtOAc in hexane) to give compound 3c (361 mg, 59% yield) as light brown foam.

1H NMR (400 MHz, DMSO-$d_6$) δ ppm 1.38-1.46 (m, 9 H), 2.03 (s, 3 H), 4.05-4.48 (m, 4 H), 6.71 (s, 2 H), 6.80 (s, 1 H), 6.82 (s, 1 H), 10.07 (s, 1 H). LCMS (M+H)$^+$ 378.

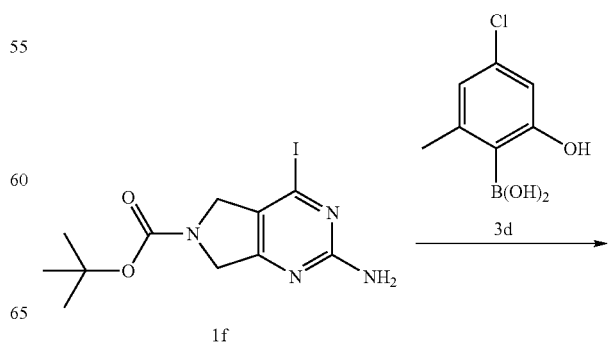

1f

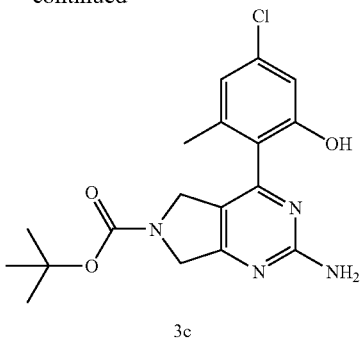

3c

Compound 3d 5-chloro-2,3-dimethyl-phenolboronic acid

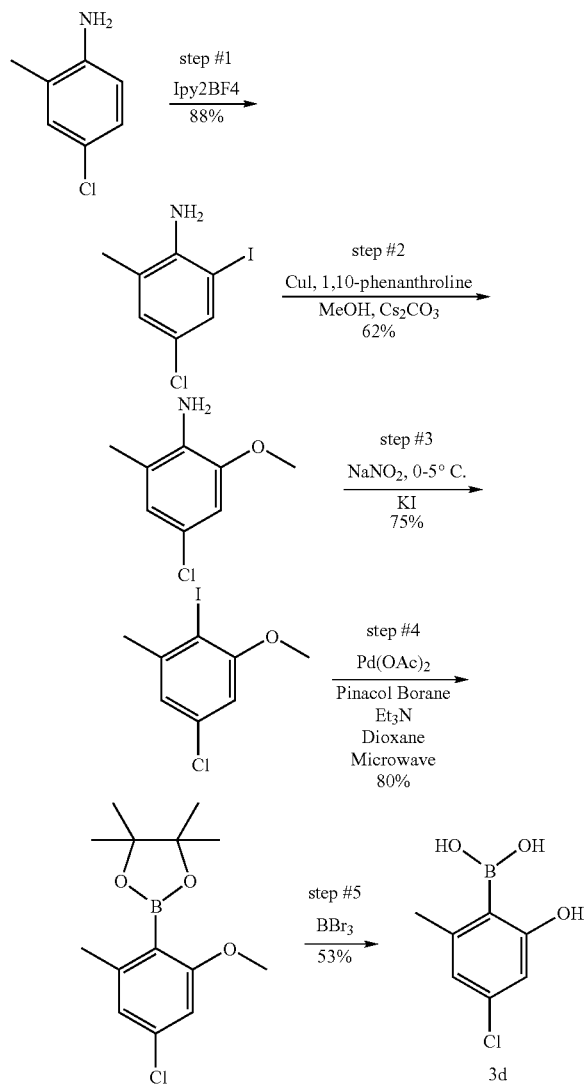

Step#1 procedure: To a clear solution of SM (5.46 mL, 45 mmol, 1.0 eq) in DCM (300 mL) at ice-NaCl bath was added Ipy$_2$BF$_4$ (20.3 g, 53.4 mmol, 1.20 eq). The resulting solution was stirred at the 0° C. bath and was then warmed slowly to rt. The reaction turned slowly from orange solution to orange suspension. The reaction was then stirred at rt overnight. The reaction was diluted with DCM (200 mL), and washed with aqueous saturated Na$_2$S$_2$O$_3$. The organic layer was collected, dried over Na$_2$SO$_4$, filtered, and concentrated. The residue was columned on silica gel to afford 10.50 g of the desired product as a brown solid in 88% yield. $^1$H NMR (400 MHz, CDCl$_3$-d) δ ppm 4.05 (br. s., 2 H), 7.02 (d, J=2.27 Hz, 1 H), 7.50 (d, J=2.27 Hz, 1 H).

Step#2 procedure: A mixture of SM (1.00 g, 3.74 mmol, 1.0 eq), CuI (73 mg, 0.374 mmol, 0.10 eq), 1,10-phenanthroline (139 mg, 0.748 mmol, 0.20 eq), Cs$_2$CO$_3$ (2.49 g, 7.48 mmol, 2.0 eq), MeOH (10 mL) was reacted under Microwave conditions (120° C., 2 h, stirring). The LC-MS indicated that the reaction was complete and the majority of the compound is the desired product. The reaction was repeated ten times, each time in 1 gram scale. All these four reaction was combined, diluted with MeOH and EtOAc. The mixture was passed through celite to remove insoluble stuff. The black filtrate was concentrated on the reduced pressure. The residue was column on silica gel using 9:1 to 4:1 heptane/EtOAc to afford 4.0 g (totally four run) of the desired product as a brown solid in 62.3% yield.

Step#3 procedure: At 0° C., to a suspension of SM (2.68 g, 15.6 mmol, 1.0 eq) in 25 mL conc. HCl (37%) was added a solution of NaNO$_2$ (2.27 g, 31.2 mmol, 2.0 eq) in 25 mL water. After being stirred at 0° C. for 10 min, an orange suspension was obtained forming diazonium salts compound. A solution of KI (10.4 g, 62.5 mmol, 4.0 eq) in water (50 mL) was added into the diazonium salt. During the addition, lots of solid stuff was generated.

The reaction was then stirred overnight at rt. After being stirred at rt overnight, the reaction was diluted with 300 mL EtOAc. The organic layer was collected and washed with 1.0 M Na$_2$S$_2$O$_3$. The organic layer was then dried over Na$_2$SO$_4$, filtered, and concentrated. The residue was columned on ISCO (10% EtOAc in Heptane) to afford 3.30 g of the desired product in 75% yield as a yellow solid. $^1$H NMR (400 MHz, CDCl$_3$-d) δ ppm 2.45 (s, 3 H), 3.88 (s, 3 H), 6.64 (d, J=1.76 Hz, 1 H), 6.91 (d, J=1.76 Hz, 1 H).

Step#4 procedure: To a 20 mL Microwave vial were added Pd(OAc)$_2$ (39.7 mg, 0.177 mmol, 0.10 eq), SM (500 mg, 1.77 mmol, 1.0 eq), dioxane (12 mL), Pinacol borane (0.514 mL, 3.54 mmol, 2.0 eq), Et$_3$N (0.74 mL, 5.31 mmol, 3.0 eq), and phosphine ligand (124 mg, 0.354 mmol, 0.20 eq). The mixture was purged with N2 and reacted in Microwave 120° C. for 30 min. The reaction was diluted with EtOAc (100 mL), filtered through celite. The filtrate was washed with brine (100 mL). The organic layer was dried and concentrated. The residue was columned on ISCO using 10% EtOAc/Heptane to afford 4.00 g of the desired product in 80% yield as a white yellow solid. $^1$H NMR (400 MHz, CDCl$_3$-d) δ ppm 1.38 (s, 12 H), 2.32 (s, 3 H), 3.76 (s, 3 H), 6.64 (d, J=1.51 Hz, 1 H), 6.76 (d, J=1.01 Hz, 1 H).

Step#5 procedure: To a solution of SM (1.50 g, 5.02 mmol) in 20 anhydrous dichloromethane at 0° C. was added Boron tribromide (12.6 mL, 12.6 mml, 2.5 eq, 1.0 M in DCM) slowly over 5 minutes. After stirring for 15 minutes at 0° C., the reaction was complete by HPLC, and was poured into 20 mL ice water. The biphasic mixture was stirred vigorously, and the aqueous phase was brought to pH=~10 with 1 M NaOH (10 mL). The organic layer was separated, and discarded. The aqueous phase was acidified to pH=~3 with 1 M HCl, white precipitates were generated, filtered, and dried at 60° C. under house vacuum to afford 500 mg (53% yield) of the desired product as a white solid.

Example 4

2-amino-N-bicyclo[1.1.1]pent-1-yl-4-{2,4-dichloro-6-[2-(4-fluoro-1H-pyrazol-1-yl)ethoxy]phenyl}-5,7-dihydro-6H-pyrrolo[3,4-d]pyrimidine-6-carboxamide A solution of compound 1b (in 3 mL of DMF) and TEA (1 mL, 7 mmol) were added to a solution of compound 4a (200 mg, 0.49 mmol) in DMF (5 mL). The mixture was heated at 70° C. for 3 h. The reaction was cooled down to room temperature. Water (30 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→10% CH$_3$OH in EtOAc) to give compound 4 (161 mg, 63.5% yield) as an oil. This oil was lyophilized to a white solid. $^1$H NMR (400 MHz, DMSO-d$_6$) δ ppm 1.94 (s, 6 H), 2.34 (s, 1 H), 3.65 (d, J=13.14 Hz, 1 H), 3.93 (d, J=13.14 Hz, 1 H), 4.20-4.28 (m, 2 H), 4.30-4.43 (m, 4 H), 6.79 (s, 2 H), 6.89 (br. s., 1 H), 7.23-7.29 (m, 2 H), 7.34 (d, J=1.77 Hz, 1 H), 7.36 (d, J=4.55 Hz, 1 H). LCMS (M+H)$^+$ 519.

Anal. Calcd for C$_{23}$H$_{22}$Cl$_2$FN$_7$O$_2$.1H$_2$O: C, 51.50; H, 4.51; N, 18.28. Found: C, 51.81; H, 4.34; N, 18.02.

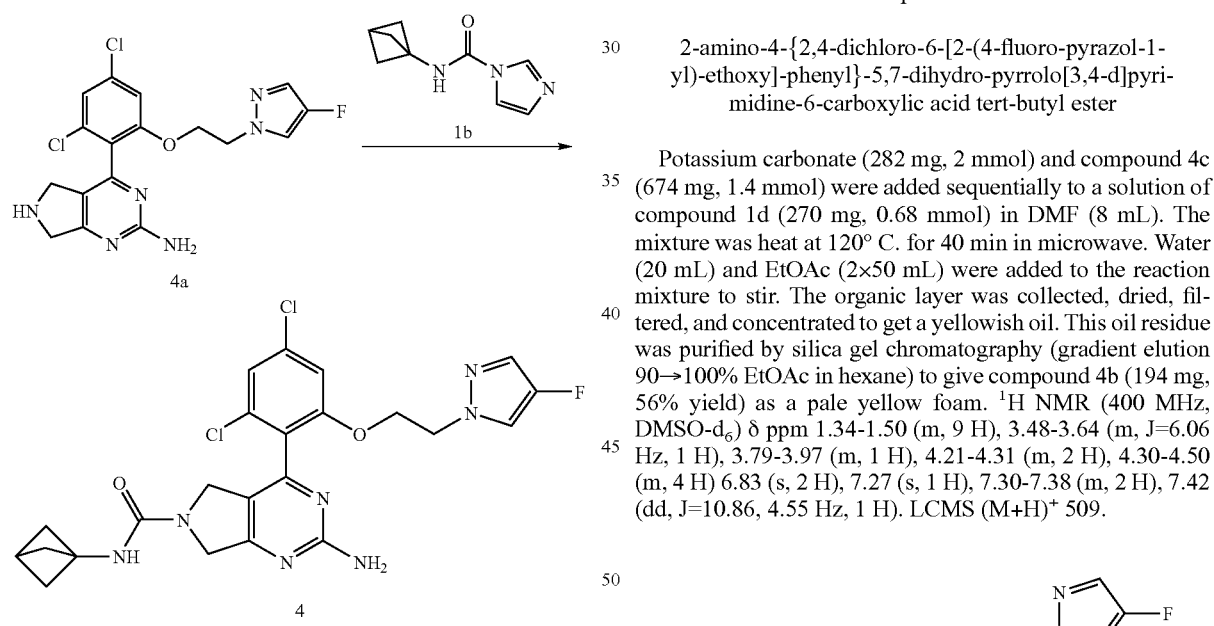

Compound 4a

4-{2,4-dichloro-6-[2-(4-fluoro-pyrazol-1-yl)-ethoxy]-phenyl}-6,7-dihydro-5H-pyrrolo[3,4-d]pyrimidin-2-ylamine Hydrogen chloride (2.4 mL, 9.8 mmol, 4M in dioxane) was added to a solution of compound 4b (249 mg, 0.49 mmol) in CH$_3$OH (10 mL). The mixture was stirred at room temperature for 12 h and monitored by LC/MS. The solvent was evaporated to afford compound 4a as a light yellow solid residue. This crude residue was used for the synthesis of compound 1 without further purification.

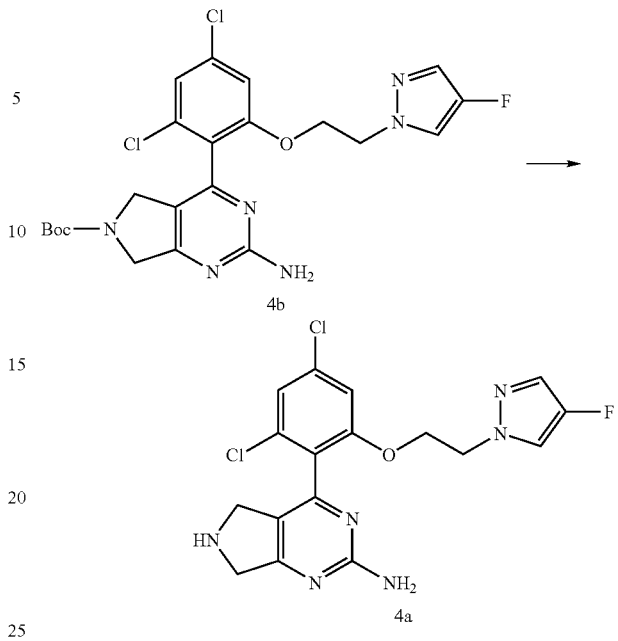

Compound 4b

2-amino-4-{2,4-dichloro-6-[2-(4-fluoro-pyrazol-1-yl)-ethoxy]-phenyl}-5,7-dihydro-pyrrolo[3,4-d]pyrimidine-6-carboxylic acid tert-butyl ester Potassium carbonate (282 mg, 2 mmol) and compound 4c (674 mg, 1.4 mmol) were added sequentially to a solution of compound 1d (270 mg, 0.68 mmol) in DMF (8 mL). The mixture was heat at 120° C. for 40 min in microwave. Water (20 mL) and EtOAc (2×50 mL) were added to the reaction mixture to stir. The organic layer was collected, dried, filtered, and concentrated to get a yellowish oil. This oil residue was purified by silica gel chromatography (gradient elution 90→100% EtOAc in hexane) to give compound 4b (194 mg, 56% yield) as a pale yellow foam. $^1$H NMR (400 MHz, DMSO-d$_6$) δ ppm 1.34-1.50 (m, 9 H), 3.48-3.64 (m, J=6.06 Hz, 1 H), 3.79-3.97 (m, 1 H), 4.21-4.31 (m, 2 H), 4.30-4.50 (m, 4 H) 6.83 (s, 2 H), 7.27 (s, 1 H), 7.30-7.38 (m, 2 H), 7.42 (dd, J=10.86, 4.55 Hz, 1 H). LCMS (M+H)$^+$ 509.

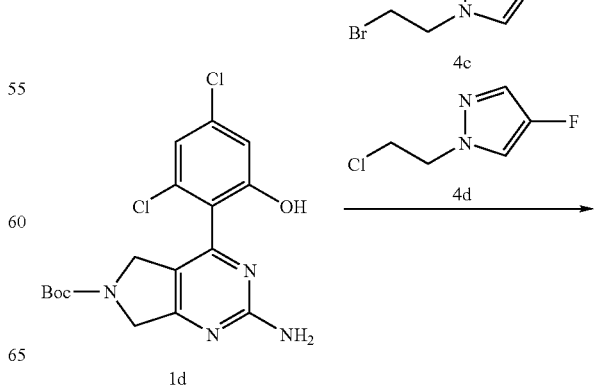

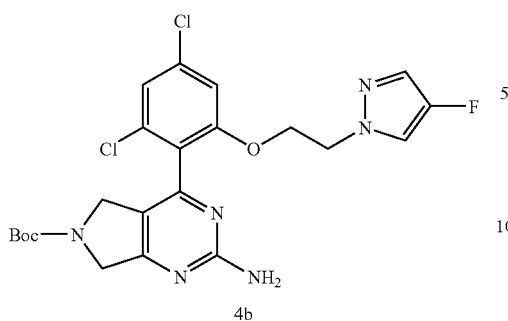

4b

Synthesis of compounds 4c and 4d 4-fluoro-1-(2-bromo-ethyl)-1H-pyrazole and 4-fluoro-1-(2-chloro-ethyl)-1H-pyrazole Sodium hydride (700 mg, 17.4 mmol, 60% dispersion in mineral oil was added to a solution of fluoropyrazole (1000 mg, 11.6 mmol) in DMF (7 mL) at room temperature. The mixture was stirred at room temperature for 40 min. The mixture was then canulated to a 1-bromo-2-chloroethane (2000 mg, 13.9 mmol, in 1 mL of DMF). The mixture was heated to 60° C. for 12 h. Water (50 mL) was added to the reaction mixture and THF (2×200 mL) was added to extract the aqueous solution. The combined organic layer was dried, filtered, and concentrated to get a waxy oil residue. LC/MS and $^1$H-NMR indicated it's the mixture of two products, compound 4c and compound 4d (1000 mg, 57.4% yield).

Synthesis of fluoropyrazole: Fluoropyrazole was prepared and isolated by modifying the method described in Organic Letters 1995, 3, p 239.

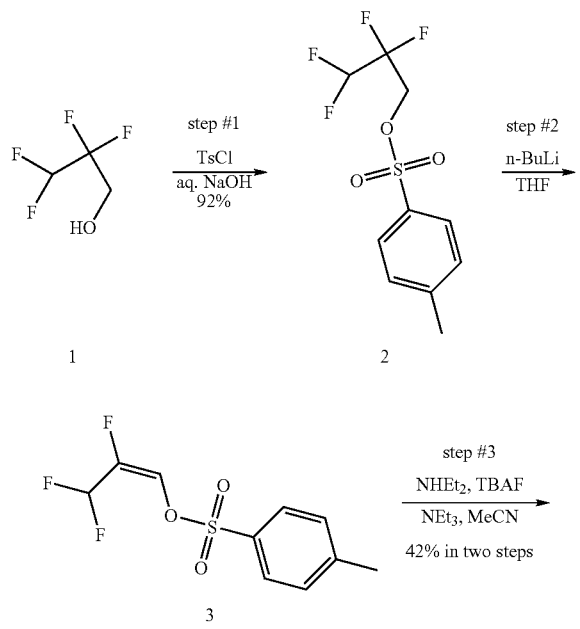

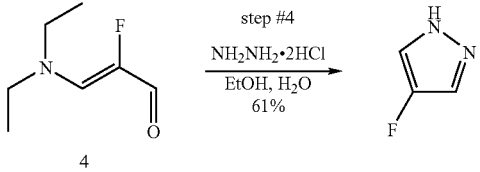

Step#1 Procedure:

To a solution of compound 1 (750 g, 5.7 mol) and Et$_3$N (948 mL, 6.816 mol) in CH$_2$Cl$_2$ (2 L) was added TsCl (1295.4 g, 6.8 mol) at 0° C. in portions. The resulting mixture was stirred at room temperature overnight. TLC (petroleum ether/EtOAc=5:1) indicated the reaction was complete. Brine (5 L) was added, and the mixture was extracted with CH$_2$Cl$_2$ (3×10 L). The combined organic layers were washed with brine (2×5 L), dried over Na$_2$SO$_4$ and concentrated in vacuo to give crude product, which was purified by column chromatography (silica gel, petroleum ether/EtOAc from 20:1 to 5:1) to yield compound 2 (1500 g, 92%) as a white solid.

Step#2 Procedure:

To a solution of compound 2 (100 g, 0.35 mmol) in THF (1.5 L) was added n-BuLi (336 ml, 0.8 mol) dropwise at −85° C. Then the mixture was stirred at −85° C. for another 10 minutes. The reaction mixture was quenched with 3 N aqueous HCl (300 mL) and allowed to warm to room temperature. The mixture was basified to pH=7 with saturated aqueous NaHCO$_3$ and extracted with Et$_2$O (3×5 L). The organic layer was dried over Na$_2$SO$_4$ and concentrated in vacuum to give compound 3 (53.84 g, 58%) as a brown solid, which was used for the next step directly.

Step#3 Procedure:

A solution of compound 3 (150 g, 0.5639 mol) in CH$_3$CN (500 mL) was added to a solution of NHEt$_2$ (50 g, 0.7 mol), TBAF (56.3 mL, 0.05639 mol) and Et$_3$N (78 mL, 0.6 mol) in CH$_3$CN (300 mL) at 0° C. The resulting solution was stirred at room temperature overnight. TLC (petroleum ether/EtOAc=1:1) indicated the reaction was complete. The mixture was diluted with brine (300 mL) and extracted with EtOAc (500 mL×3). The combined organic layers were dried over Na$_2$SO$_4$ and concentrated in vacuum to give crude product, which was purified by column chromatography (silica gel, petroleum ether/EtOAc=1:1) to yield compound 4 (60 g, 73%) as brown oil.

Step#4 Procedure:

A mixture of compound 4 (100 g, 0.7 mol) and NH$_2$NH$_2$.2HCl (79.6 g, 0.8 mol) in EtOH (200 mL) and H2O (150 mL) was stirred at 78° C. for 4 hours. TLC (petroleum ether/EtOAc=1:1) indicated the reaction was complete. The reaction mixture was allowed to cool to room temperature. The mixture was basified to pH=7 with saturated aqueous NaHCO$_3$ and extracted with EtOAc (3×2 L). The combined organic layers were dried over Na$_2$SO$_4$ and concentrated in vacuum to give crude product, which was purified by column chromatography (silica gel, petroleum ether/EtOAc=1:1) to yield fluoropyrazole (36.25 g, 61%) as a brown solid.

$^1$H NMR (400 MHz, dmso-d$_6$) δ ppm 7.64 (br. s., 2 H), 12.61 (br. s., 1 H).

Example 5

2-amino-N-bicyclo[1.1.1]pent-1-yl-4-{2,4-dichloro-6-[2-(4-fluoro-1H-pyrazol-1-yl)ethoxy]phenyl}-5,7-dihydro-6H-pyrrolo[3,4-d]pyrimidine-6-carboxamide A solution of compound 5a (in 3 mL of DMF) and TEA (1 mL, 7 mmol) were added to a solution of compound 4a (195 mg, 0.48 mmol) in DMF (4 mL). The mixture was heated at 70° C. for 3 h. The reaction was cooled down to room temperature. Water (30 mL) was added to the reaction mixture and EtOAc (2×50 mL) was added to extract the aqueous solution. The combined organic layer was dried, filtered, and concentrated to get a brown yellow oil. This oil residue was purified by silica gel chromatography (gradient elution 0→10% CH$_3$OH in EtOAc) to give compound 5 (192 mg, 75.5% yield) as an oil. This oil was lyophilized to a white solid. $^1$H NMR (400 MHz, dmso-d$_6$) δ ppm 3.66 (d, J=13.14 Hz, 1 H), 3.82 (br. s., 2 H), 3.98 (d, J=12.63 Hz, 1 H), 4.26 (d, J=4.04 Hz, 2 H), 4.30-4.38 (m, 2 H), 4.42 (br. s., 2 H), 6.83 (s, 2 H), 6.99 (s, 1 H), 7.23 (d, J=4.29 Hz, 1 H), 7.29 (d, J=1.52 Hz, 1 H), 7.35 (d, J=1.77 Hz, 1 H), 7.37 (d, J=4.55 Hz, 1 H). LCMS (M+H)$^+$ 534.

Anal. Calcd for C$_{20}$H$_{17}$Cl$_2$F$_4$N$_7$O$_2$.0.25H$_2$O: C, 44.58; H, 3.27; N, 18.20. Found: C, 44.87; H, 3.34; N, 17.86.

compound 6a (71 mg, 0.17 mmol) in DMF (3 mL). The mixture was heated at 100° C. for 60 min in microwave. Water (20 mL) and EtOAc (100 mL) were added to the reaction mixture to stir. The organic layer was collected, dried, filtered, and concentrated to get a yellowish oil. This oil residue was purified by preparative HPLC to give compound 6 (30 mg, 33% yield) as a white solid. $^1$H NMR (400 MHz, DMSO-d$_6$) δ ppm 1.56 (t, J=18.95 Hz, 3 H), 3.43-3.55 (m, 2 H), 3.69 (d, J=13.14 Hz, 1 H), 4.00 (d, J=12.88 Hz, 1 H), 4.20-4.28 (m, 2 H), 4.31-4.37 (m, 2 H), 4.40-4.47 (m, 2 H), 6.69 (s, 1 H), 6.81 (s, 2 H), 7.26 (d, J=4.29 Hz, 1 H), 7.28 (d, J=1.77 Hz, 1 H), 7.34 (d, J=1.77 Hz, 1 H), 7.36 (d, J=4.80 Hz, 1 H). LCMS (M+H)$^+$ 530. Anal. Calcd for C$_{21}$H$_{20}$Cl$_2$F$_3$N$_7$O$_2$.1.75H$_2$O: C, 44.89; H, 4.22; N, 17.45. Found: C, 45.22; H, 3.90; N, 17.12.

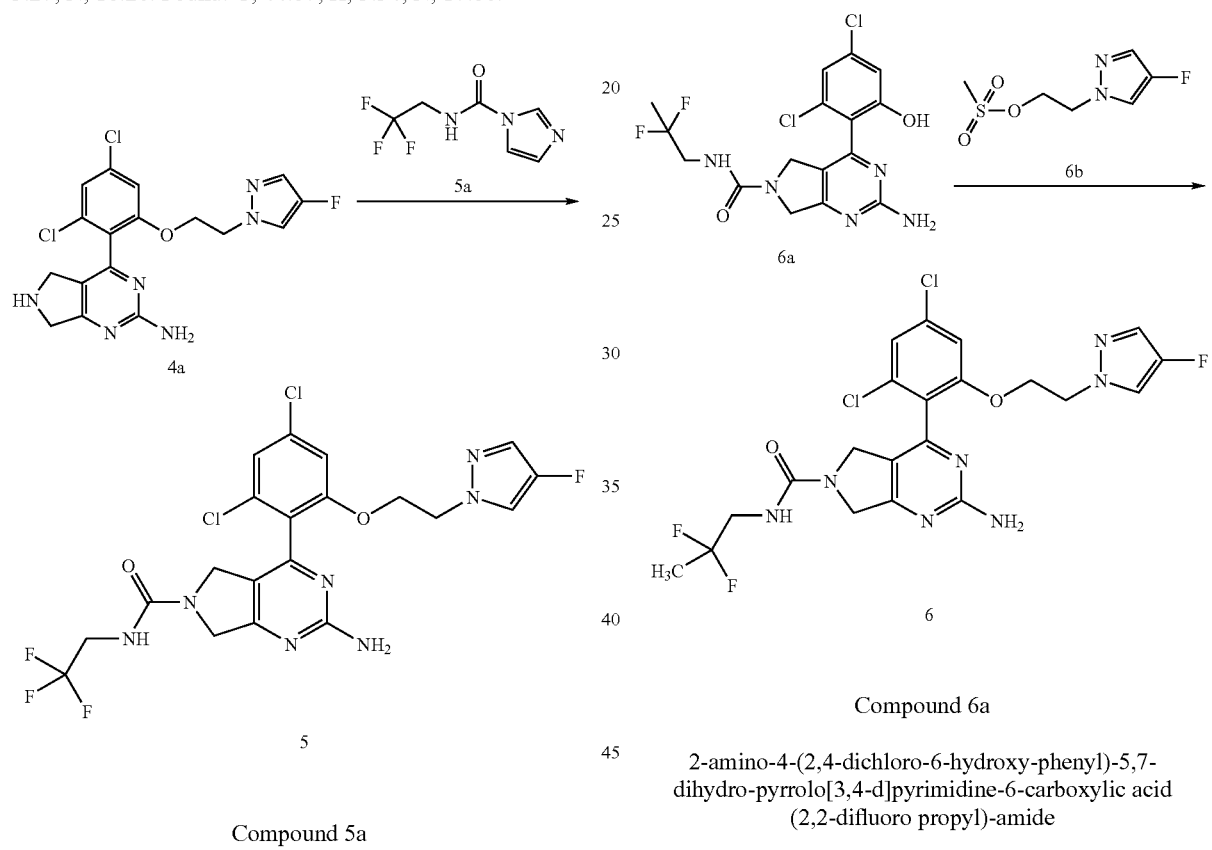

Compound 5a

1-[(Z)-methyliminomethyl]-3-(2,2,2-trifluoro-ethyl)-1-vinyl-urea

TEA (1.3 mL, 0.8 mmol) was added to a solution of 2,2,2-trifluoroethylamine (72 mg, 1 mmol) and 1,1'-carbonyldiimidazole (135 mg, 0.8 mmol) in DMF (4 mL) (clear colorless solution). The solution was used for the synthesis of compound 5 without further isolation of compound 5a.

Example 6

2-amino-N-bicyclo[1.1.1]pent-1-yl-4-{2,4-dichloro-6-[2-(4-fluoro-1H-pyrazol-1-yl)ethoxy]phenyl}-5,7-dihydro-6H-pyrrolo[3,4-d]pyrimidine-6-carboxamide Potassium carbonate (120 mg, 0.85 mmol) and compound 6b (89 mg, 0.4 mmol) were added sequentially to a solution of Compound 6a 2-amino-4-(2,4-dichloro-6-hydroxy-phenyl)-5,7-dihydro-pyrrolo[3,4-d]pyrimidine-6-carboxylic acid (2,2-difluoro propyl)-amide Sodium carbonate solution (7.8 mL, 2M, 15.5 mmol) were added to a solution of compound 1g (1.07 g, 5.17 mmol) and compound III(B)-2 (1.98 g, 5.17 mmol) in 1,4-dioxane (25 mL). The mixture was purged with N2 for 15 min, then tetrakis (triphenylphsophino) palladium (0) (597 mg, 0.517 mmol) was added. The resulting mixture was stirred at 85° C. for 3 hours. The reaction mixture was filtered through Celite pad and washed well with MeOH. The filtrate was concentrated by vacuum. The residue was partitioned between EtOAc (2×500 mL) and brine (100 mL). The organic layer was dried, filtered, and concentrated to get a brown oil. Isolation by preparative HPLC to afford compound 6a as a white solid (305 mg, 14% yield).

$^1$H NMR (400 MHz, DMSO-d$_6$) δ ppm 1.54 (t, J=19.07 Hz, 3 H), 3.46 (br. s., 2 H), 4.21 (br. s., 2 H), 4.47 (s, 2 H), 6.73-6.84 (m, 2 H), 6.84-6.89 (m, 1 H), 6.97 (d, J=1.77 Hz, 1 H), 7.16 (d, J=2.02 Hz, 1 H), 10.69 (br. s., 1 H). LCMS (M+H)$^+$: 418.0, 420.0.

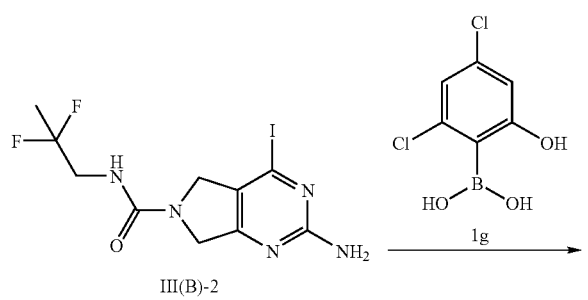

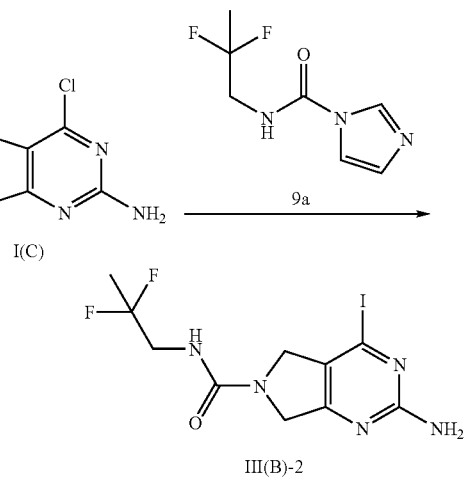

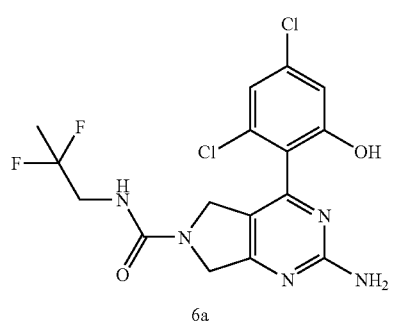

Compound 6b

Compound III(B)-2:

2-amino-4-iodo-5,7-dihydro-pyrrolo[3,4-d]pyrimidine-6-carboxylic acid (2,2-difluoro-propyl)-amide Iodotirmethylsilane (25 mL, 176 mmol) was added to a suspension of compound I(C) (8.36 g, 24.7 mmol) in ACN (200 mL) at room temperature. The mixture was refluxed at 90° C. for 3 h. The reaction mixture was cooled to rt, and then quenched with MeOH (10 mL), concentrated by vacuum. The residue was treated with Et$_2$O (100 mL), and the precipate was collected by filtration and washed well with ether to give the Hi salt of 4-Iodo-6,7-dihydro-5H-pyrrolo[3,4-d]pyrimidin-2-ylamine as a brown color solid (14.4 g, 81%). This crude product was ready to use for next reaction without further purification.

$^1$H NMR (400 MHz, DMSO-d$_6$) δ ppm 4.25 (t, J=4.80 Hz, 1 H), 4.29-4.47 (m, 3 H), 6.02 (br. s., 2 H), 9.42 (br. s., 1 H). LCMS (M+H)$^+$: 263.0.

A solution of compound 9a (in 2 mL of DMF) and TEA (0.6 mL, 4.6 mmol) were added to a solution of 4-Iodo-6,7-dihydro-5H-pyrrolo[3,4-d]pyrimidin-2-ylamine HI salt (590 mg, 1.1 mmol) in DMF (5 mL). The mixture was heated at 65° C. for 2 h. The reaction was cooled down to room temperature. Water (50 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→100% EtOAc in dichloromethane) to give compound III (B)-2 as a white solid (195 mg, 82% yield). $^1$H NMR (400 MHz, DMSO-d$_6$) δ ppm 1.50-1.60 (m, 3 H), 3.51 (br. s., 2 H), 4.32 (s, 2 H), 4.46 (d, J=6.06 Hz, 2 H). LCMS (M+H)$^+$: 384.0.

Methanesulfonic acid 2-(4-fluoro-pyrazol-1-yl)-ethyl ester

Methanesulfonyl chloride (16.8 g, 11.4 mL, 147 mmol) was added to a solution of compound 6a (13.4 g, 98 mmol), diisopropylamine (34.3 mL, 196 mmol), and 4-(dimethylamino)-pyridine (1.2 g, 9.78 mmol) in dichloromethane (245 mL) in an ice bath. The reaction was warm to room temperature and stirred at room temperature for 2 h. Water (50 mL) was added to quench the reaction. The organic layer was dried, filtered, and concentrated to get a brown oil. This oil residue was purified by silica gel chromatography (0→60% EtOAc in hexane) to give compound 6b (19.5 g, 96% yield) as a yellowish oil. $^1$H NMR (400 MHz, CDCl$_3$-d) δ ppm 2.89 (s, 3 H), 4.33-4.38 (m, 2 H), 4.53-4.59 (m, 2 H), 7.38 (d, J=1.52 Hz, 1 H), 7.40 (d, J=1.01 Hz, 1 H).

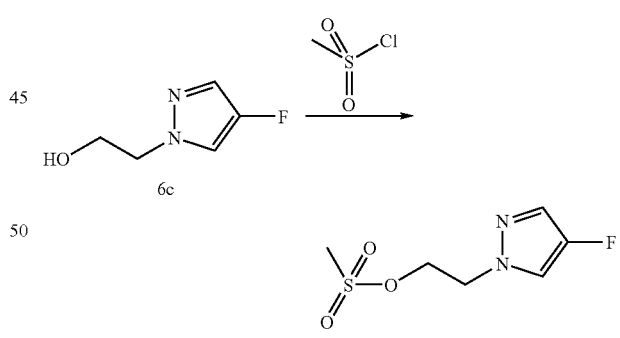

Preparation of Compound 6c

2-(4-Fluoro-pyrazol-1-yl)-ethanol

Sodium hydride (13.8 g, 0.35 mol, 60% dispersion in mineral oil) was added to a solution of fluoropyrazole (20 g, 0.23 mol) in DMF (200 mL) 0° C. The mixture was stirred at room temperature for 1 h and then 2-bromo-ethanol (43 g, 0.35 mol) was added dropwisely at 0° C. The resulting mixture was stirred at 40° C. for 12 h. TLC (petroleum ether/EtOAc=1:1)

indicated the reaction was complete. The mixture was quenched with saturated aqueous NH₄Cl (200 mL). Then DMF was removed in vacuo and the residue was partitioned between Et₂O (1000 mL) and H₂O (1000 mL). The aqueous layer was extracted with more Et₂O (4×1 L). The combined organic layers were dried over Na₂SO₄ and concentrated in vacuum to give compound 6c (20 g, 66%) as a yellow oil. $^1$H NMR (400 MHz, DMSO-$d_6$) δ ppm 3.69 (t, J=5.56 Hz, 2 H), 4.04 (t, J=5.56 Hz, 2 H), 4.90 (br. s., 1 H), 7.43 (d, J=4.29 Hz, 1 H), 7.81 (d, J=4.55 Hz, 1 H).

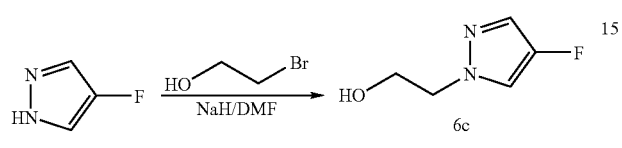

Example 7

2-amino-N-bicyclo[1.1.1]pent-1-yl-4-{4-chloro-2-[2-(4-fluoro-1H-pyrazol-1-yl)ethoxy]-6-methylphenyl}-5,7-dihydro-6H-pyrrolo[3,4-d]pyrimidine-6-carboxamide A solution of compound 1b (in 3 mL of DMF) and TEA (1 mL, 7 mmol) were added to a solution of compound 7a (186 mg, 0.48 mmol) in DMF (5 mL). The mixture was heated at 70° C. for 3 h. The reaction was cooled down to room temperature. Water (50 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→10% CH₃OH in EtOAc) to give compound 7 (195 mg, 82% yield) as an oil. This oil was lyophilized to a white solid. 1H NMR (400 MHz, MeOD) δ ppm 2.05 (s, 6 H), 2.06 (s, 3 H), 2.37 (s, 1 H), 3.71 (d, J=12.63 Hz, 1 H), 3.96 (dd, J=13.01, 1.39 Hz, 1 H), 4.23-4.36 (m, 4 H), 4.43-4.55 (m, 2 H), 6.97 (s, 1 H), 6.98 (s, 1 H), 7.24 (d, J=4.55 Hz, 1 H), 7.26 (d, J=4.29 Hz, 1 H). LCMS (M+H)⁺ 499.

Anal. Calcd for $C_{24}H_{25}ClFN_7O_2 \cdot 0.25H_2O$: C, 57.89; H, 5.06; N, 19.69. Found: C, 57.31; H, 5.11; N, 19.44.

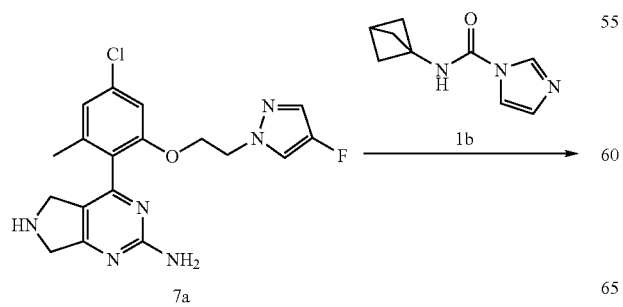

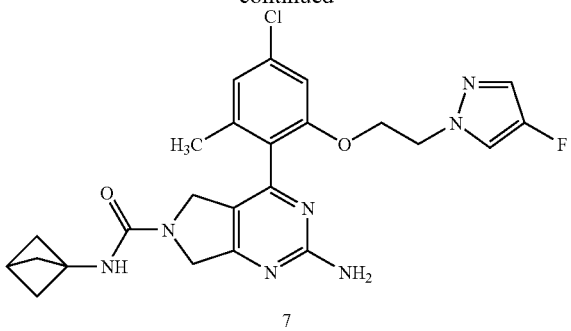

Compound 7a

4-{4-chloro-2-[2-(4-fluoro-pyrazol-1-yl)-ethoxy]-6-methyl-phenyl}-6,7-dihydro-5H-pyrrolo[3,4-d]pyrimidin-2-ylamine Hydrogen chloride (2.4 mL, 9.5 mmol, 4M in dioxane) was added to a solution of compound 7b (234 mg, 0.48 mmol) in CH₃OH (10 mL). The mixture was stirred at room temperature for 12 h and monitored by LC/MS. The solvent was evaporated to afford compound 7a as a light yellow solid residue. This crude residue was used for the synthesis of compound 7 without further purification.

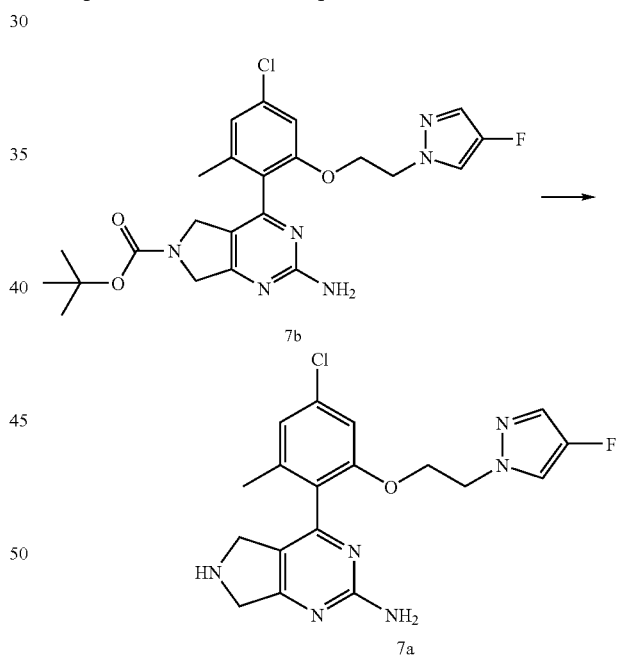

Compound 7b 2-amino-4-{4-chloro-2-[2-(4-fluoro-pyrazol-1-yl)-ethoxy]-6-methyl-phenyl}-5,7-dihydro-pyrrolo[3,4-d]pyrimidine-6-carboxylic acid tert-butyl ester Potassium carbonate (154 mg, 1.1 mmol) and compound 6b (120 mg, 0.6 mmol) were added sequentially to a solution of compound 3c (84 mg, 0.22 mmol) in DMF (2 mL). The mixture was heated at 100° C. for 40 min. in microwave. Water (10 mL) and EtOAc (50 mL) were added to the reaction mixture to stir. The organic layer was collected, dried, filtered, and concentrated to get a yellowish oil. This oil residue was purified by silica gel chromatography (90→100% EtOAc in hexane) to give compound 7b (66 mg, 60% yield) as a light yellow foam. $^1$H NMR (400 MHz, DMSO-d$_6$) δ ppm 1.44 (s, 9 H), 2.00 (s, 3 H), 3.50 (dd, J=23.49, 13.39 Hz, 1 H), 3.83 (dd, J=25.52, 12.88 Hz, 1 H), 4.17-4.31 (m, 4 H), 4.33-4.41 (m, 2 H), 6.70 (s, 2 H), 6.99 (s, 1 H), 7.04 (s, 1 H), 7.28 (dd, J=18.44, 4.29 Hz, 1 H), 7.42 (dd, J=10.74, 4.42 Hz, 1 H). LCMS (M+H)$^+$ 489. Anal. Calcd for C$_{23}$H$_{26}$ClFN$_6$O$_3$.0.5H$_2$O.0.25 CH$_3$CO$_2$CH$_2$CH$_3$: C, 55.44; H, 5.62; N, 16.16. Found: C, 55.78; H, 5.49; N, 15.93.

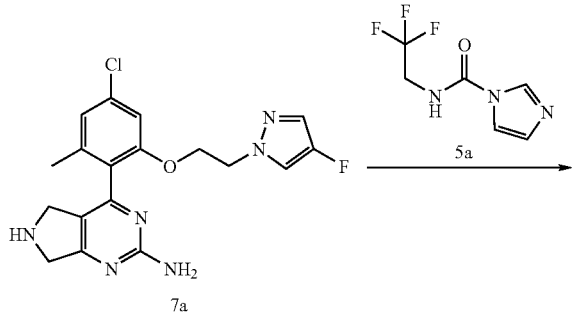

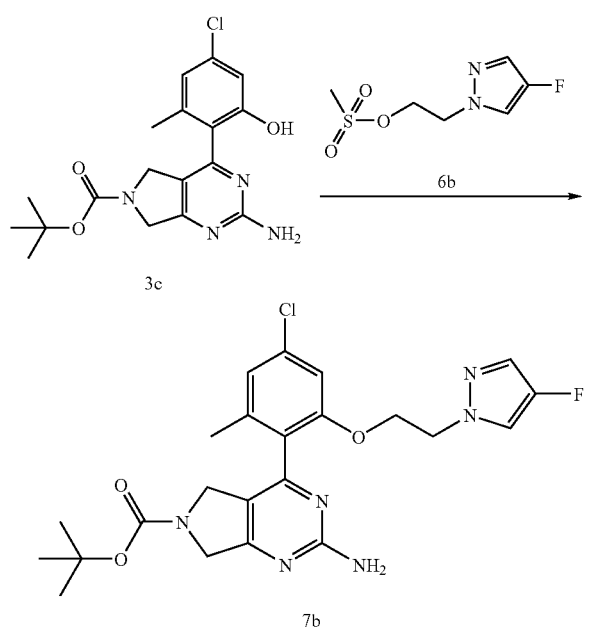

Example 8

2-amino-4-{4-chloro-2-[2-(4-fluoro-1H-pyrazol-1-yl)ethoxy]-6-methylphenyl}-N-(2,2,2-trifluoroethyl)-5,7-dihydro-6H-pyrrolo[3,4-d]pyrimidine-6-carboxamide A solution of compound 5a (in 5 mL of DMF) and TEA (2 mL, 14 mmol) were added to a solution of compound 7a (504 mg, 1.3 mmol) in DMF (5 mL). The mixture was heated at 70° C. for 3 h. The reaction was cooled down to room temperature. Water (50 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→10% CH$_3$OH in EtOAc) to give compound 8 (470 mg, 70% yield) as an oil. This oil was lyophilized to a white solid. $^1$H NMR (400 MHz, DMSO-d$_6$) δ ppm 2.01 (s, 3 H), 3.61 (d, J=12.88 Hz, 1 H), 3.75-3.85 (m, 2 H), 3.91 (d, J=12.63 Hz, 1 H), 4.26 (dd, J=12.88, 3.79 Hz, 4 H), 4.36-4.44 (m, 2 H), 6.73 (s, 2 H), 6.92 (s, 1 H), 7.01 (s, 1 H), 7.06 (s, 1 H), 7.23 (d, J=4.04 Hz, 1 H), 7.37 (d, J=4.55 Hz, 1 H). LCMS (M+H)$^+$ 514.

Anal. Calcd for C$_{21}$H$_{20}$ClF$_4$N$_7$O$_2$.1H$_2$O: C, 47.42; H, 4.17; N, 18.43. Found: C, 47.54; H, 3.85; N, 18.13.

Example 9

2-amino-4-{4-chloro-2-[2-(4-fluoro-1H-pyrazol-1-yl)ethoxy]-6-methylphenyl}-N-(2,2-difluoropropyl)-5,7-dihydro-6H-pyrrolo[3,4-d]pyrimidine-6-carboxamide A solution of compound 9a (in 3 mL of DMF) and diisopropylethylamine (1 mL) were added to a solution of compound 7a (136 mg, 0.35 mmol) in DMF (5 mL). The mixture was heated at 75° C. for 2 h. The reaction was cooled down to room temperature. Water (50 mL) was added to the reaction mixture and EtOAc (2×100 mL) was added to extract the aqueous solution. The combined organic layer was dried, filtered, and concentrated to get a brown yellow oil. This oil residue was purified by silica gel chromatography (gradient elution 0→10% CH$_3$OH in EtOAc) to give compound 9 (171 mg, 96% yield) as an oil. This oil was lyophilized to a white solid. $^1$H NMR (400 MHz, DMSO-d$_6$) δ ppm 1.56 (t, J=18.95 Hz, 3 H), 2.01 (s, 3 H), 3.40-3.52 (m, 2 H), 3.65 (d, J=13.14 Hz, 1 H), 3.92 (d, J=12.63 Hz, 1 H), 4.26 (dd, J=11.62, 3.28 Hz, 4 H), 4.37-4.45 (m, 2 H) 6.66 (s, 1 H), 6.70 (s, 2 H) 7.01 (s, 1 H), 7.06 (s, 1 H), 7.26 (d, J=4.04 Hz, 1 H), 7.36 (d, J=4.55 Hz, 1 H). LCMS (M+H)$^+$ 511.

Anal. Calcd for C$_{22}$H$_{23}$ClF$_3$N$_7$O$_2$.0.25H$_2$O: C, 51.37; H, 4.60; N, 19.06. Found: C, 51.34; H, 4.65; N, 18.70.

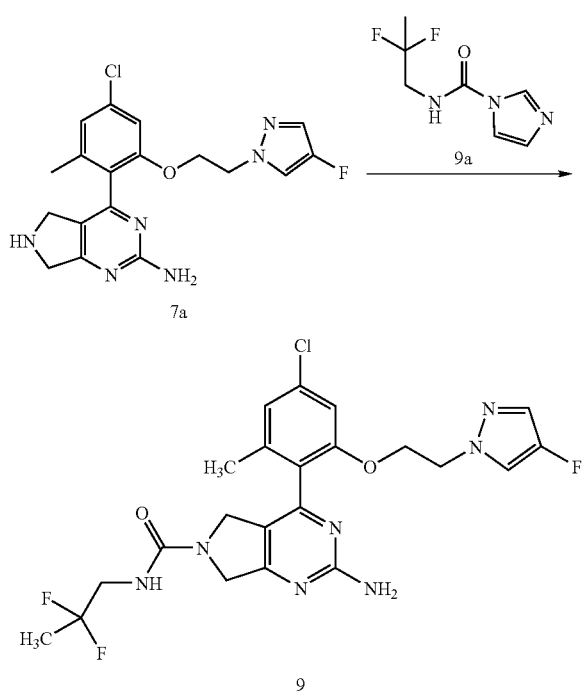

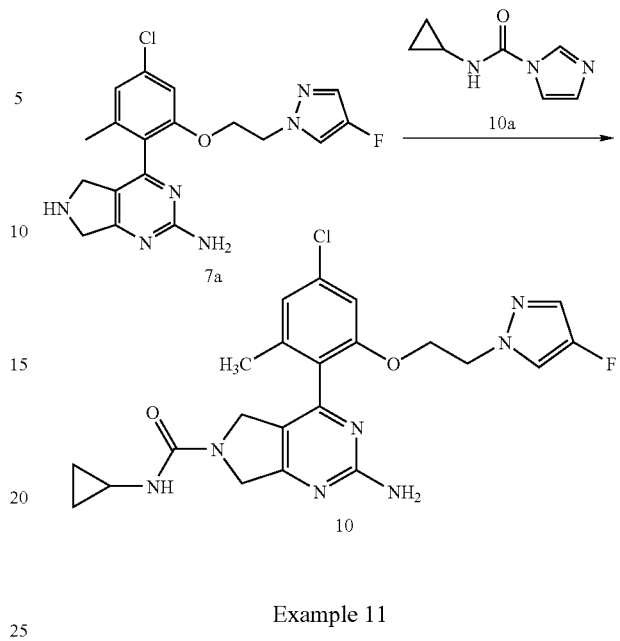

Compound 9a

Imidazole-1-carboxylic acid (2,2-difluoro-propyl)-amide

TEA (1.3 mL, 0.8 mmol) was added to a solution of 2,2-difluoropropylamine hydrochloride (82 mg, 0.62 mmol) and 1,1'-CARBONYLDIIMIDAZOLE (114 mg, 0.7 mmol) in DMF (3 mL) (clear colorless solution). The solution was used for the synthesis of compound 5 without further isolation of compound 9.

Example 10

2-amino-N-cyclopropyl-4-{2,4-dichloro-6-[2-(4-fluoro-1H-pyrazol-1-yl)ethoxy]phenyl}-5,7-dihydro-6H-pyrrolo[3,4-d]pyrimidine-6-carboxamide Compound 10 was prepared in a manner similar to Example 9 except that imidazole-1-carboxylic acid cyclopropylamide (10a) was substituted for imidazole-1-carboxylic acid (2,2-difluoro-propyl)-amide (compound 9a). Compound 10 was obtained as a white solid (26 mg, 40%). $^1$H NMR (400 MHz, DMSO-d$_6$) δ ppm 0.36-0.44 (m, 2 H), 0.49-0.63 (m, 2 H), 1.19-1.28 (m, 1 H), 3.65 (d, J=13.14 Hz, 1 H), 3.93 (d, J=13.14 Hz, 1 H), 4.21-4.28 (m, 2 H), 4.29-4.44 (m, 4 H), 6.35 (s, 1 H), 6.78 (s, 2 H), 7.20-7.29 (m, 2 H), 7.33 (d, J=1.77 Hz, 1 H), 7.35 (d, J=4.55 Hz, 1 H). LCMS (M+H)$^+$ 493.

Anal. Calcd for C$_{21}$H$_{20}$Cl$_2$FN$_7$O$_2$.1.25H$_2$O.0.25 CH$_3$COOH: C, 48.74; H, 4.47; N, 18.50. Found: C, 48.75; H, 4.08; N, 18.24.

Example 11

2-amino-4-{2,4-dichloro-6-[2-(4-cyano-1H-pyrazol-1-yl)ethoxy]phenyl}-N-(2,2-difluoropropyl)-5,7-dihydro-6H-pyrrolo[3,4-d]pyrimidine-6-carboxamide Compound 11b (136 mg, 0.88 mmol) was added to a mixture of 6a (147 mg, 0.35 mmol) and cesium carbonate (400 mg, 1.23 mmol) in DMSO (3 mL). The resulting mixture was heated at 90° C. for 12 h. Sat. sodium carbonate solution (50 mL) was added to the mixture and EtOAc (2×50 mL) was added to extract the aqueous solution. The combined organic layer was dried, filtered, and concentrated to get a brown oil. Isolation by preparative HPLC gave compound 11 (18 mg, 20%). $^1$H NMR (400 MHz, DMSO-d6) δ ppm 1.56 (t, J=19.07 Hz, 3 H), 3.48 (d, J=6.06 Hz, 1 H), 3.67 (br. s., 1 H), 3.92-4.08 (m, 2 H), 4.36-4.50 (m, 6 H), 6.70 (d, J=2.02 Hz, 1 H), 6.78 (s, 2 H), 7.31 (d, J=1.77 Hz, 1 H), 7.34 (d, J=1.77 Hz, 1 H), 7.81 (s, 1 H), 8.19 (s, 1 H). LCMS (M+H)$^+$ 537.

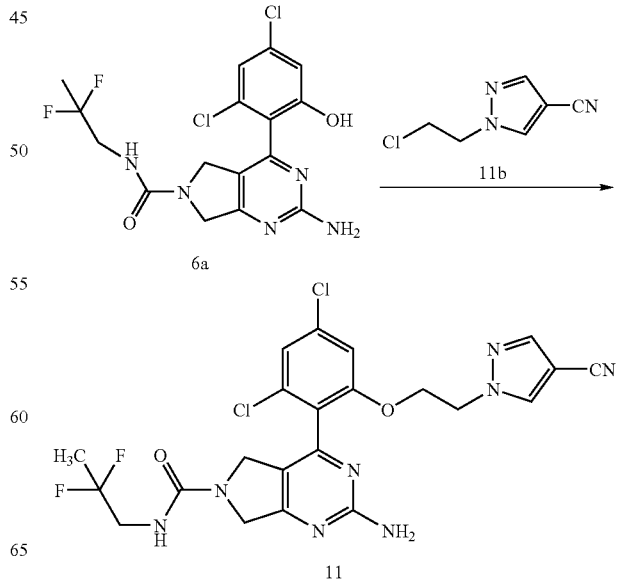

Compound 11b

1-(2-chloro-ethyl)-1H-pyrazole-4-carbonitrile

Thionyl chloride (0.14 mL, 1.84 mmol) was added to a suspension of compound 1c (160 mg, 0.92 mmol) in DCM (4 mL) at ~0° C. (ice/water bath). The resulting mixture was stirred at 0° C. and warmed to room temperature for 90 min while suspension become yellowish solution. The reaction mixture was concentrated by vacuum. The residue was partitioned between EtOAc (300 mL) and sat. NaHCO$_3$ solution (50 mL) and brine (50 mL). The organic layer was dried (Na$_2$SO$_4$), filtered, and concentrated by vacuum to give compound 11b as yellow grease (140 mg, 98%). This solid was used for the next step reaction without further purification. 1H NMR (400 MHz, DMSO-d6) δ ppm 3.96-4.08 (m, 2 H), 4.47-4.56 (m, 2 H), 8.12 (s, 1 H), 8.64 (s, 1 H).

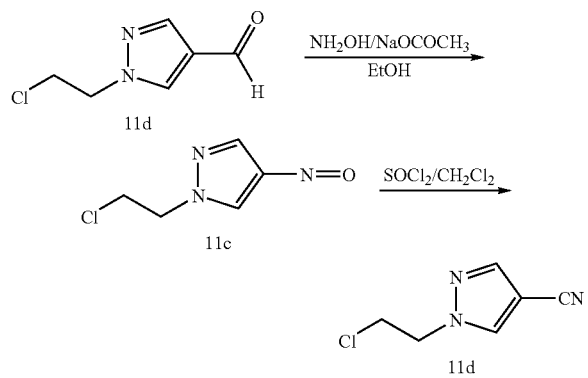

Preparation of Compound 11c

1-(2-Chloro-ethyl)-4-nitrosomethyl-1H-pyrazole

Hydroxyamine hydrochloride (114 mg, 1.6 mmol) was added to a solution of compound 11d (166 mg, 1.1 mmol) and sodium acetate (174 mg, 2.1 mmol) in EtOH (4 mL). The resulting mixture was stirred at 90° C. for 90 min. The reaction mixture was partitioned between EtOAc (300 mL) and H$_2$O (50 mL) and brine (50 mL). The organic layer was dried, filtered, and concentrated to give compound 11c as white solid (164 mg, 90%). $^1$H NMR (400 MHz, dmso-d6) δ ppm 4.00 (t, J=5.68 Hz, 2 H), 4.49 (t, J=5.68 Hz, 2 H), 7.36 (s, 1 H), 7.85 (s, 1 H), 8.33 (s, 1 H), 11.26 (s, 1 H). LCMS (M+H)$^+$: 174

Preparation of Compound 11d

1-(2-Chloro-ethyl)-4-nitrosomethyl-1H-pyrazole

Compound 11d was prepared in a manner similar to compounds 4c and 4d except that 4-carbaldehydepyrazole was substituted for 4-fluoropyrazole in Example 4.

Example 12

2-amino-4-{2-[2-(4-bromo-1H-pyrazol-1-yl)ethoxy]-4,6-dichlorophenyl}-N-cyclopropyl-5,7-dihydro-6H-pyrrolo[3,4-d]pyrimidine-6-carboxamide 4-Bromopyrazole (141 mg, 1 mmol) was added to a solution of compound 12a (142 mg, 0.32 mmol), K$_2$CO$_3$ (265 mg, 1.92 mmol) and KI (106 mg, 0.64 mmol) in DMF (2 mL). The resulting mixture was heated at 130° C. 1 h in microwave. The reaction mixture was partitioned between EtOAc (300 mL) and H$_2$O (50 mL). The organic layer was dried, filtered, and concentrated to get a brown oil. Isolation by preparative HPLC gave compound 12 as a white solid (85 mg, 48%). $^1$H NMR (400 MHz, DMSO-d$_6$) δ ppm 0.34-0.46 (m, 2 H), 0.48-0.59 (m, 2 H), 2.53-2.57 (m, 1 H), 3.73 (d, J=11.12 Hz, 1 H), 3.96 (dd, J=13.14, 2.02 Hz, 1 H), 4.26-4.50 (m, 6 H), 6.37 (br. s., 1 H), 6.78 (s, 2 H), 7.27 (d, J=1.77 Hz, 1 H), 7.33-7.35 (m, 1 H), 7.38 (s, 1 H), 7.48-7.55 (m, 1 H). LCMS (M+H)$^+$: 552.

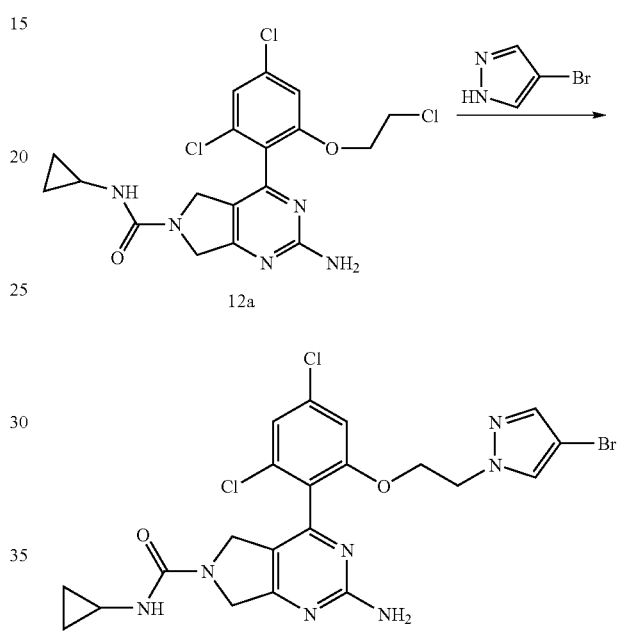

Compound 12a

2-amino-4-[2,4-dichloro-6-(2-chloro-ethoxy)-phenyl]-5,7-dihydro-pyrrolo[3,4-d]pyrimidine-6-carboxylic acid cyclopropylamide 1-Bromo-2-chloroethane (0.4 mL, 4.2 mmol) was added to a solution of compound 2a (800 mg, 2.1 mmol) and potassium carbonate (872 mg, 6.3 mmol) in DMF (8 mL). The resulting mixture was heated at 50° C. for 12 h. The reaction mixture was filtered off to remove carbonate salt and washed well with EtOAc. The filtrate was then partitioned between EtOAc (200 ml) and sat. NaHCO$_3$ (50 ml) and brine (50 ml). The organic layers were dried (Na$_2$SO$_4$), then concentrated by vacuum. This oil residue was purified by silica gel chromatography (gradient elution 0→10% CH$_3$OH in dichloromethane) to afford compound 12a (786 mg, 85%). $^1$H NMR (400 MHz, DMSO-d$_6$) d ppm 0.32-0.43 (m, 2 H), 0.47-0.58 (m, 2 H), 3.69-3.86 (m, 1 H), 4.00-4.12 (m, 2 H), 4.19 (d, J=13.14 Hz, 2 H), 4.23-4.31 (m, 2 H), 4.32-4.45 (m, 2 H), 6.42 (d, J=2.78 Hz, 1 H), 6.80 (s, 2 H), 7.38 (d, J=1.77 Hz, 1 H), 7.96 (s, 1 H). LCMS (M+H)$^+$ 444.

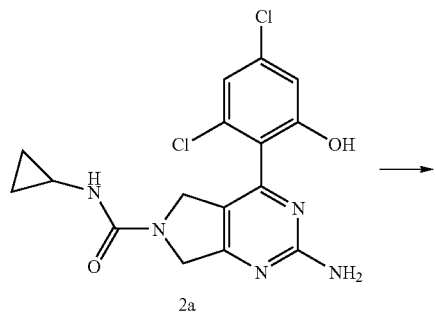

2a

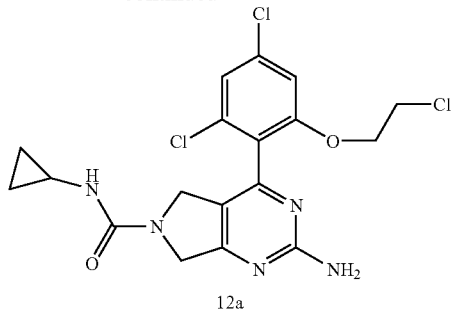

12a

Examples 13-16 were prepared using methods similar to those described in the above examples.

TABLE 1

| Ex # | Structure | Name, analytical data and synthetic method |
|---|---|---|
| 13 | 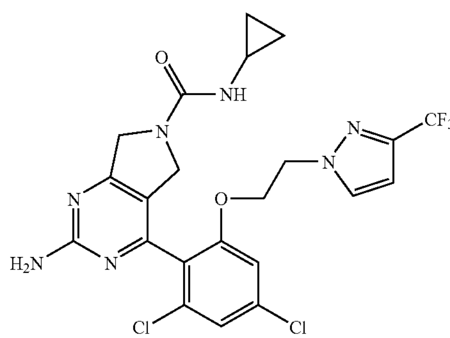 | 2-amino-N-cyclopropyl-4-(2,4-dichloro-6-{2-[3-(trifluoromethyl)-1H-pyrazol-1-yl]ethoxy}phenyl)-5,7-dihydro-6H-pyrrolo[3,4-d]pyrimidine-6-carboxamide $^1$H NMR (400 MHz, DMSO-$d_6$) δ ppm 0.31-0.42 (m, 2 H), 0.47-0.56 (m, 2 H), 2.48-2.55 (m, 1 H), 3.65 (d, J = 13.14 Hz, 1 H), 3.97 (d, J = 13.14 Hz, 1 H), 4.30-4.37 (m, 2 H), 4.40 (br. s., 2 H), 4.46 (t, J = 4.67 Hz, 2 H), 6.34 (br. s., 1 H), 6.45 (d, J = 2.02 Hz, 1 H), 6.81 (s, 2 H), 7.26 (d, J = 1.77 Hz, 1 H), 7.30-7.38 (m, 2 H) Method of Example 12 |
| 14 | 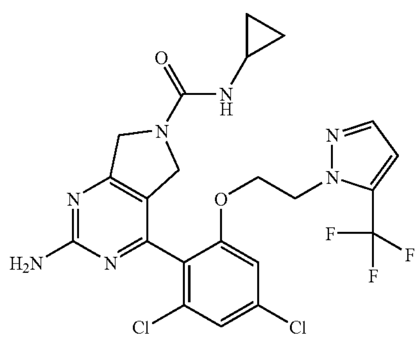 | 2-amino-N-cyclopropyl-4-(2,4-dichloro-6-{2-[5-(trifluoromethyl)-1H-pyrazol-1-yl]ethoxy}phenyl)-5,7-dihydro-6H-pyrrolo[3,4-d]pyrimidine-6-carboxamide $^1$H NMR (400 MHz, DMSO-$d_6$) δ ppm 0.35-0.47 (m, 2 H), 0.55 (d, J = 7.07 Hz, 2 H), 2.52-2.59 (m, 1 H), 3.20 (d, J = 13.14 Hz, 1 H), 3.78 (d, J = 12.88 Hz, 1 H), 4.30 (s, 2 H), 4.34-4.54 (m, 4 H), 6.31 (br. s., 1 H), 6.55 (d, J = 1.77 Hz, 1 H), 6.70 (s, 2 H), 7.32 (s, 2 H), 7.45 (d, J = 1.52 Hz, 1 H) Method of example 12 |
| 15 | 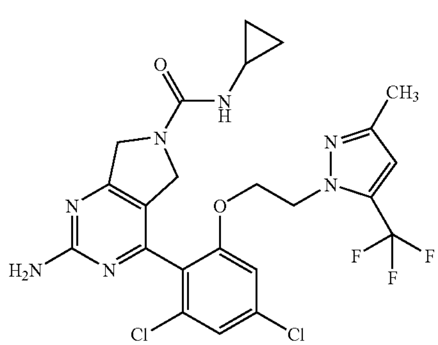 | 2-amino-N-cyclopropyl-4-(2,4-dichloro-6-{2-[3-methyl-5-(trifluoromethyl)-1H-pyrazol-1-yl]ethoxy}phenyl)-5,7-dihydro-6H-pyrrolo[3,4-d]pyrimidine-6-carboxamide $^1$H NMR (400 MHz, DMSO-$d_6$) δ ppm 0.28-0.42 (m, 2 H), 0.51 (d, J = 7.07 Hz, 2 H), 1.78 (s, 3 H), 2.52-2.56 (m, 1 H), 3.43 (br. s., 1 H), 3.90 (d, J = 13.14 Hz, 1 H), 4.20-4.37 (m, 3 H), 4.36-4.48 (m, 3 H), 6.22 (s, 1 H), 6.29 (s, 1 H), 6.82 (s, 2 H), 7.28 (d, J = 1.77 Hz, 1 H), 7.34 (d, J = 1.77 Hz, 1 H) Method of example 12. |

TABLE 1-continued

| Ex # | Structure | Name, analytical data and synthetic method |
|---|---|---|
| 16 | (structure shown) | 2-amino-N-cyclopropyl-4-(2,4-dichloro-6-{2-[5-methyl-3-(trifluoromethyl)-1H-pyrazol-1-yl]ethoxy}phenyl)-5,7-dihydro-6H-pyrrolo[3,4-d]pyrimidine-6-carboxamide $^1$H NMR (400 MHz, DMSO-$d_6$) δ ppm 0.35 (br. s., 2 H), 0.47 (br. s., 2 H), 2.06 (s, 3 H), 2.45-2.50 (m, 1 H), 3.10 (d, J = 1.01 Hz, 1 H), 3.72 (d, J = 2.02 Hz, 1 H), 4.24 (d, J = 20.72 Hz, 3 H), 4.34 (br. s., 3 H), 6.20-6.33 (m, 2 H), 6.64 (s, 2 H), 7.18-7.29 (m, 2 H) Method of example 12 |

HSP-90 Biochemical Assay

Compounds of the present invention were evaluated for potency against HSP-90 using a SPA (scintillation proximity assay) competition binding assay. Either full length or N-terminal HSP-90 that contains a 6-His tag on its C-terminus binds to copper on Yttrium-silicate scintillant beads via the His-tag. Tritiated propyl-Geldanamycin (pGA), whose structure is shown below, is an analog of a natural inhibitor of HSP-90 called Geldanamycin. Tritiated pGA, which contains a tritiated propyl-amine group added at the #17 position, binds HSP-90 and brings the isotope into proximity with the beads. 17-n-propylamino-Geldanamycin can be prepared as described in U.S. Pat. No. 4,261,989, which is incorporated herein by reference. A second tritiated compound that can also be used in this assay is shown below and is designated as Compound A.

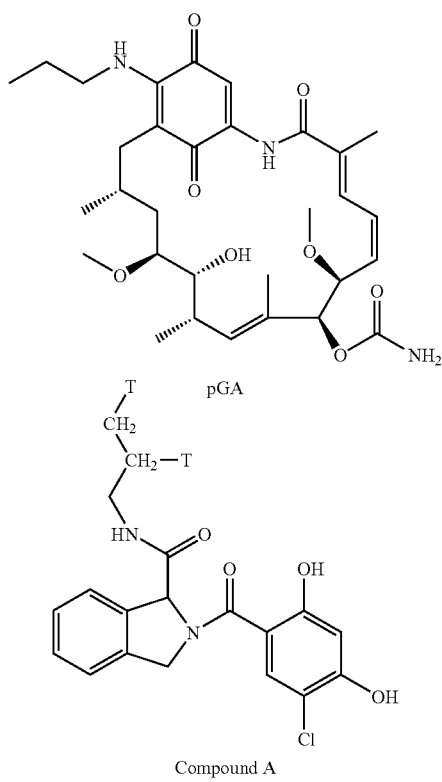

Compound A

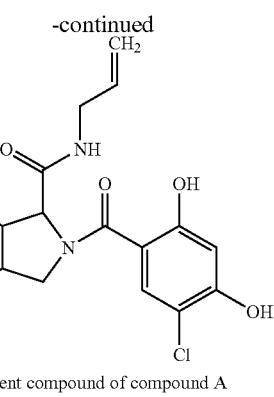

parent compound of compound A

The "T" in the structure of Compound A above indicates the position of the labeled tritiated hydrogen atoms. This compound has a $K_d$ of 40 nM and can be prepared as follows. Compound A can be prepare from the parent compound of Compound A, (N-allyl-2-(5-chloro-2,4-dihydroxybenzoyl) isoindoline-1-carboxamide) as described in the following. Allylamine (2.5 mL, 5 mmol, 2M in THF) was added to a solution of Boc(R,S)-1,3-dihydro-2H-isoindole carboxylic acid (263 mg, 1 mmole), diisopropylethyl amine (0.9 mL, 5 mmol), and O-(7-azabenzotriazol-1-yl)-N,N,N',N'-tetramethyluronium phosphorus pentafloride (HATU) (420 mg, 1.1 mmol) in 5 mL of DMF under a nitrogen atmosphere. The reaction was allowed to stir at room temperature for 12 hours. Saturated NaHCO$_3$ (30 mL) was added to the reaction mixture to quench the reaction. EtOAc (2×50 mL) was then added to extract the aqueous solution. Dry EtOAc layer over Na$_2$SO$_4$. The Na$_2$SO$_4$ was filtered off and the filtrate was evaporated to give a brown oil residue. The residue was purified by silica gel chromatography (gradient elution 40→50% EtOAc in hexanes) to give the desired intermediate product (321 mg, quantitative yield) tert-butyl 1-[(allylamino)carbonyl]-1,3-dihydro-2H-isoindole-2-carboxylate.

Hydrogen chloride (3 mL, 12 mmol; 4 M in dioxane) was added to a solution of tert-butyl 1-[(allylamino)carbonyl]-1,3-dihydro-2H-isoindole-2-carboxylate (1 mmol) in DCM (5 mL) at room temperature. The reaction was heated and stirred at room temperature for 12 hours. The reaction mixture was evaporated to give an oil residue. The residue (N-allylisoindoline-1-carboxamide) was used for the next step reaction without further purification.

N-allylisoindoline-1-carboxamide (1 mmol) was then added to a solution of 5-chloro-2,4-bis(methoxymethoxy)

benzoic acid (which can be prepared as shown in WO 2006/117669) (340 mg, 1.2 mmol), 4-methylmorpholine (2.2 mL, 20 mmol), N-(3-dimethylaminopropyl)-N'-ethylcarbodiimide hydrochloride (460 mg, 2.4 mmol), and 1-hydroxy benzotriazole (330 mg, 2.4 mmol) in 12 mL of DMF under a nitrogen atmosphere. The reaction was allowed to stir at room temperature for 12 hours. $H_2O$ (50 mL) was added to the reaction mixture to quench the reaction. EtOAc (2×100 mL) was then added to extract the aqueous solution. Dry EtOAc layer over $Na_2SO_4$. The $Na_2SO_4$ was filtered off and the filtrate was evaporated to give a brown oil residue. The residue was purified by silica gel chromatography (gradient elution 50→60% EtOAc in hexanes) to give the desired intermediate product (423 mg, 91.8% yield) N-allyl-2-[5-chloro-2,4-bis(methoxymethoxy)benzoyl]isoindoline-1-carboxamide.

Hydrogen chloride (4 mL, 16 mmol; 4 M in dioxane) was added to a solution of N-allyl-2-[5-chloro-2,4-bis(methoxymethoxy)benzoyl]isoindoline-1-carboxamide (392 mg, 0.85 mmol) in DCM (5 mL). The reaction was stirred at room temperature for 12 hours. The reaction mixture was neutralized with saturated $NaHCO_3$ (aq) and then extracted with EtOAc (2×50 mL). The combined organic layers were dried, filtered, and evaporated to give the desired final product as the parent compound (N-allyl-2-(5-chloro-2,4-dihydroxybenzoyl)isoindoline-1-carboxamide) as a white solid (221 mg, 69.7% yield). $^1$H NMR (400 MHz, DMSO-$d_6$) δ ppm 3.57 (d, J=79.33 Hz, 2 H), 4.65-4.93 (m, 1 H), 4.97-5.19 (m, 1 H), 5.42-5.70 (m, 1 H), 5.68-5.95 (m, 1 H), 6.40-6.71 (m, 1 H), 6.92 (s, 1 H), 7.15-7.67 (m, 4 H), 8.28 (s, 1 H), 10.06 (s, 1 H), 10.40 (s, 1 H). Anal. Calcd for $C_{19}H_{17}ClN_2O_4$: C, 61.21; H, 4.60; N, 7.51. Found: C, 61.02; H, 4.63; N, 7.36.

Once the parent compound was made, Compound A was prepared using standard hydrogenation methods using tritium gas.

The beta signal emitted from the isotope excites the scintillant, which creates a measurable signal. As competitive compounds are added to the assay mixture, they compete with bound tritiated pGA or Compound A at the ATP-binding site on the N-terminal of HSP-90. When a compound displaces the labeled pGA or Compound A, the signal is reduced (the beta-particles are no longer in proximity with the bead). This reduction in signal is used to quantify the extent to which the inhibitor/compound is competitive with pGA or Compound A.

The SPA assay for $^3$H-PGA (designated G1) and Compound A (designated G2) binding to HSP-90 was performed in 96-well flat bottom white plates (Corning #3604). For G1, typical reaction solutions contained 30 nM HSP-90 and 200 nM $^3$H-PGA in binding buffer (100 mM Hepes, pH 7.5 and 150 mM KCl). For G2, typical reaction solutions contained 5 nM HSP-90 and 50 nM of Compound A. For G1, the $^3$H-PGA was first diluted to 33% label with unlabeled pGA that was synthesized and purified to give a final concentration of 200 nM. For G2, labeled Compound A was diluted with unlabeled Compound A to provide a ratio of labeled:unlabeled of 1:2 for a final concentration of 50 nM. Inhibitors were added to the HSP-90/$^3$H-PGA (or HSP-90/Compound A) solutions at eleven different concentrations for $K_i$ determinations. The range of inhibitor concentrations were 100 µM, or an appropriate range, for solid samples and 10 µM for targeted library compounds and 4 mM liquid stocks. To determine percent inhibition, the compound was tested at 1 and 10 µM. The final DMSO in the samples was 4%. Copper-Ysi beads (Amersham, #RPNQ0096) that have been diluted in binding buffer were added to each well to give a final concentration of 100 µg/well. The plates were sealed, covered with a foil-covered 10d and shaken for 30 minutes at room temperature. The beads were allowed to settle for 30 minutes after which the plates were counted using a Packard TopCount NXT instrument. This procedure has also been adapted for medium throughput using a Beckman Biomek FX. Samples were run in duplicate and on two separate days to assure an accurate value of $K_i$.

For $K_i$ determinations, the corrected cpm's (actual cpm's minus background) were plotted vs. inhibitor concentration using GraphPad Prism software. The data were fit to a generic $IC_{50}$ equation, $Y=YI/(1+[X]/IC_{50})$, where YI=Y-intercept and [X] is the competing ligand/inhibitor. The $IC_{50}$ was then used to calculate the Ki by using the Cheng-Prusoff equation:

$$Ki\{cl\} = \frac{IC_{50}\{cl\}}{1 + ([hl]/Kd\{hl\})}$$

Where cl=cold ligand concentration (varies), [hl]=concentration of hot ligand (200 nM or 50 nM) and Kd{hl}=240 nM (for $^3$H-PGA) or 40 nM (for Compound A). Error was calculated as follows: $IC_{50}$ error/$IC_{50}$ value=fractional error and fractional error*$K_i$ value=$K_i$ error.

In the cases in which inhibitor binds to HSP-90 so tightly that the population of free inhibitor molecules is significantly depleted by formation of the enzyme-inhibitor complex, the above equation is no longer valid. This is normally true when the observed $IC_{50}$ is about the same as the HSP-90 concentration. For a tight binding inhibitor, the following equation can be applied:

$$\frac{EL}{EL_o} = \frac{-(K_I^{app} + I_o - E_o) + \sqrt{(K_I^{app} + I_o - E_o)^2 + 4 \times E_o \times K_I^{app}}}{2 \times E_o}$$

$$\text{where } K_I^{app} = K_I \times \left(1 + \frac{L_o}{K_L}\right)$$

EL and $EL_o$ are the radioligand-HSP-90 complexes in the presence and absence of inhibitor, respectively. $EL/EL_o$ represents the fractional signal in the presence of inhibitor. Io, $E_o$, and $L_o$ are the inhibitor, HSP-90, and radioligand concentrations, respectively. $K_I$ is the inhibition constant for the ligand, while $K_L$ is the binding affinity constant between the enzyme (HSP-90) and the ligand.

The Ki assay data of the compound 1-16 of Examples 1-16 are listed in the following Table 2.

TABLE 2

| EX# | (G2): Ki (nM) | Akt Lum: IC$_{50}$ (µM) |
|---|---|---|
| 1 | 4.68 | 0.0384 |
| 2 | 3.38 | 0.104 |
| 3 | 3.39 | 0.0525 |
| 4 | 2.05 | 0.0164 |
| 5 | 1.69 | 0.0702 |
| 6 | 3.32 | 0.0328 |
| 7 | 3.44 | 0.0209 |
| 8 | 1.50 | 0.0370 |
| 9 | 6.27 | 0.0357 |
| 10 | 2.86 | 0.111 |
| 11 | 64.3 | 2.55 |
| 12 | 4.69 | 0.175 |
| 13 | 7.76 | 0.660 |
| 14 | 75.1 | 6.69 |
| 15 | 437 | 18.3 |
| 16 | 259 | 9.96 |

We claim:

1. A compound of formula (I)

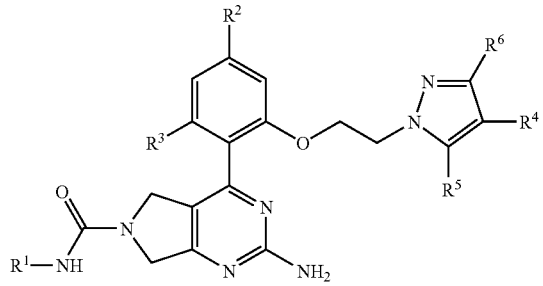

or a pharmaceutically acceptable salt thereof, wherein:

$R^1$ is selected from the group consisting of $C_1$-$C_6$ alkyl, $C_1$-$C_6$ alkyl substituted with 1 to 6 fluorine, $C_1$-$C_6$ alkyl substituted with 1 to 2 chlorine and up to six fluorine, $C_3$-$C_8$ cycloalkyl, and $C_3$-$C_8$ cycloalkyl substituted with 1 to 6 groups selected from fluorine, chlorine and $C_1$-$C_3$ alkyl;

$R^2$ and $R^3$ are independently selected from the group consisting of chlorine, fluorine, —CN, $C_1$-$C_3$ alkoxyl, $C_1$-$C_3$ alkyl and $C_1$-$C_3$ alkyl substituted with 1 to 6 fluorine;

$R^4$ is selected from the group consisting of hydrogen, fluorine, chlorine, bromine, —CN, $C_1$-$C_3$ alkyl and $C_1$-$C_3$ alkyl substituted with 1 to 6 fluorine;

$R^5$ and $R^6$ are independently selected from the group consisting of hydrogen, fluorine, chlorine, bromine, —CN, $C_1$-$C_3$ alkyl and $C_1$-$C_3$ alkyl substituted with 1 to 6 fluorine;

provided that (1) when $R^4$, $R^5$ and $R^6$ are all hydrogen, then $R^2$ and $R^3$ are not both chlorine; and (2) the compound of formula I is not any of the following compounds,

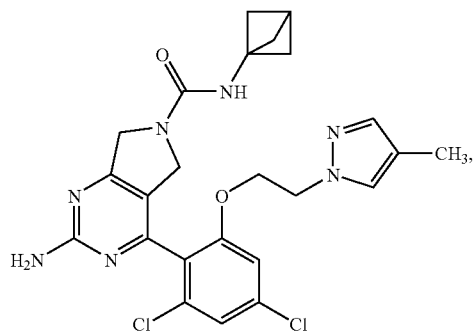

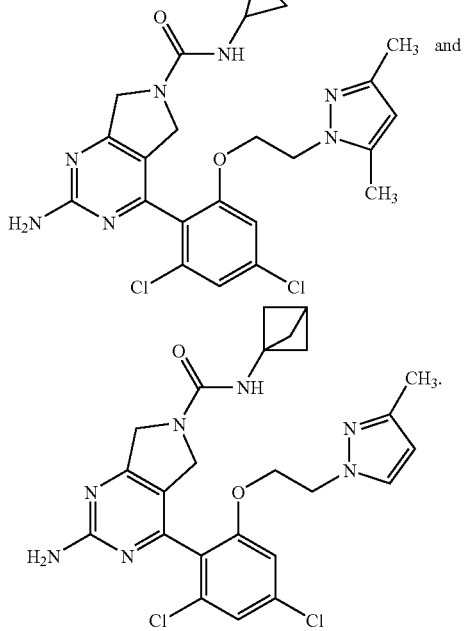

2. The compound or salt of claim 1, wherein $R^4$ is hydrogen, $R^5$ is hydrogen, $R^6$ is hydrogen, and $R^3$ is selected from the group consisting of fluorine, $C_1$-$C_3$ alkyl and $C_1$-$C_3$ alkyl substituted with 1 to 6 fluorine.

3. The compound or salt of claim 1, wherein $R^4$ is hydrogen, $R^5$ is hydrogen, $R^6$ is hydrogen, and $R^2$ is selected from the group consisting of fluorine, $C_1$-$C_3$ alkyl and $C_1$-$C_3$ alkyl substituted with 1 to 6 fluorine.

4. The compound or salt of claim 1, wherein $R^4$ is selected from fluorine, chlorine, $C_2$-$C_3$ alkyl and $C_1$-$C_3$ alkyl substituted with 1 to 6 fluorine.

5. The compound or salt of claim 1, wherein $R^4$ is fluorine or chlorine, $R^5$ is hydrogen, and $R^6$ is hydrogen.

6. The compound or salt of claim 1, wherein $R^4$ is fluorine or chlorine, $R^5$ is hydrogen, $R^6$ is hydrogen, $R^2$ is methyl or chlorine, and $R^3$ is methyl or chlorine.

7. The compound or salt of claim 1, wherein $R^5$ is $C_1$-$C_3$ alkyl substituted with 1 to 6 fluorine.

8. The compound or salt of claim 1, wherein $R^6$ is $C_1$-$C_3$ alkyl substituted with 1 to 6 fluorine.

9. The compound or salt of claim 1, wherein $R^1$ is selected from the group consisting of cyclopropyl, cyclobutyl, bicyclo[1.1.1]pent-1-yl, and $C_1$-$C_6$ alkyl substituted with 1 to 6 fluorine.

10. The compound or salt of claim 1, wherein $R^1$ is $C_3$-$C_8$ cycloalkyl or $C_3$-$C_8$ cycloalkyl substituted with 1 to 6 groups selected from fluorine, chlorine and $C_1$-$C_3$ alkyl.

11. The compound or salt of claim 1, wherein $R^1$ is $C_1$-$C_6$ alkyl, $C_1$-$C_6$ alkyl substituted with 1 to 6 fluorine, or $C_1$-$C_6$ alkyl substituted with 1 to 2 chlorine and up to six fluorine.

12. The compound or salt of claim 1, wherein $R^2$ is chlorine and $R^3$ is chlorine.

13. The compound or salt of claim 1, wherein $R^2$ is chlorine and $R^3$ is $C_1$-$C_3$ alkyl.

14. A compound selected from the group consisting of
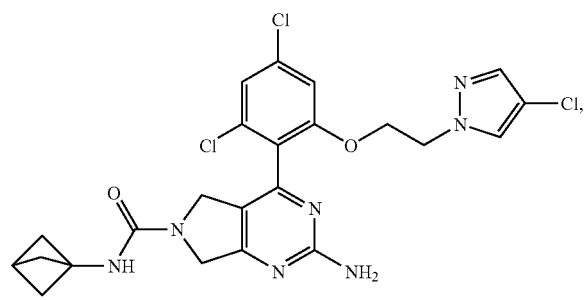
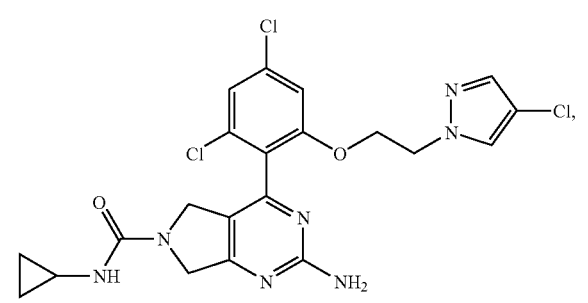
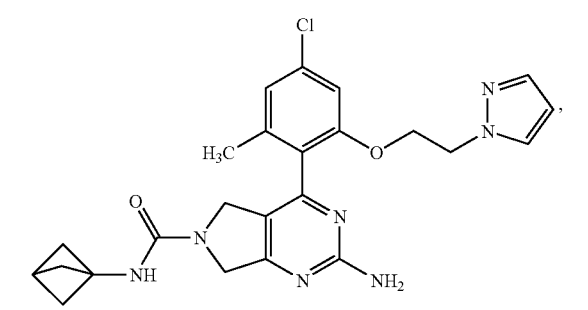
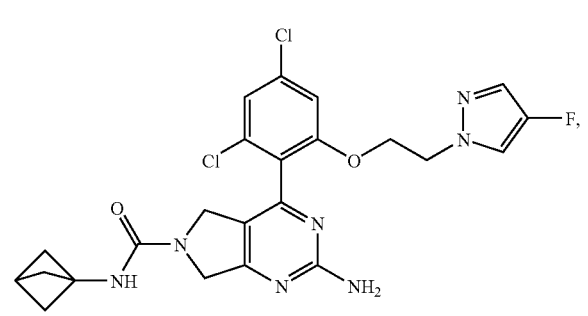
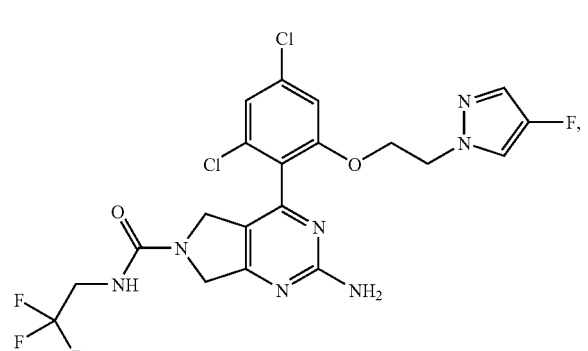
-continued
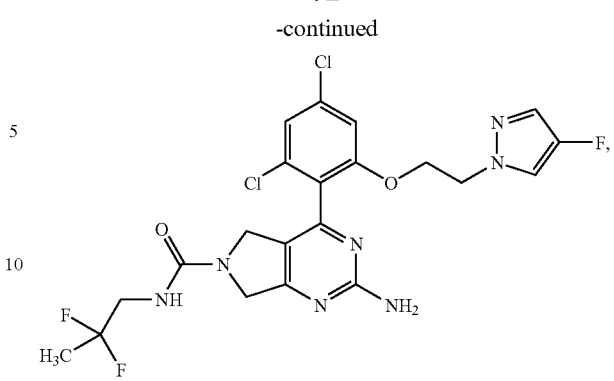
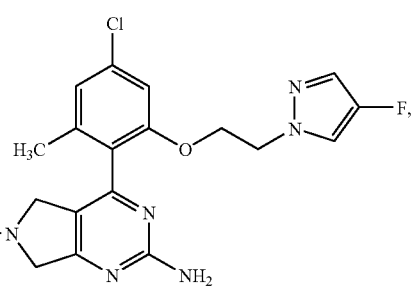
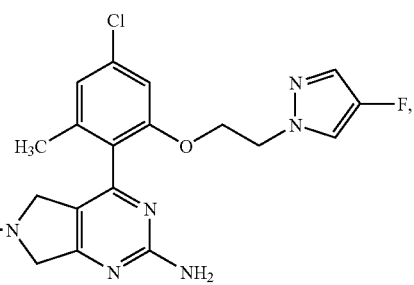
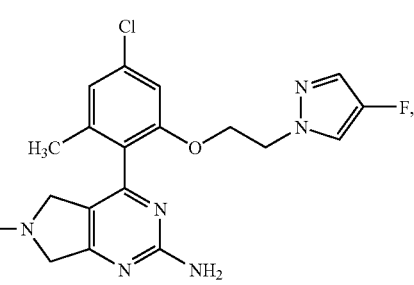
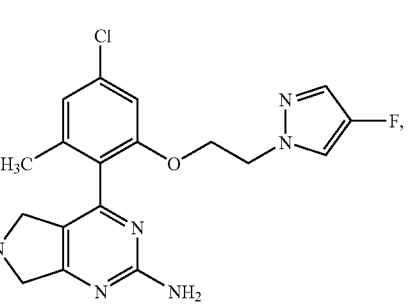

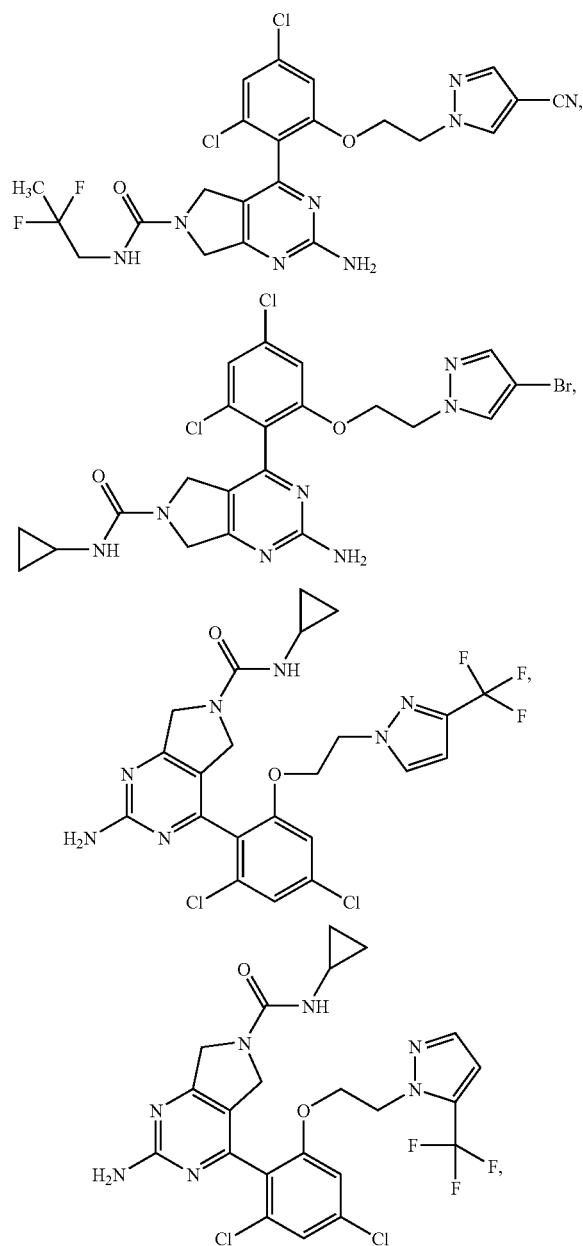
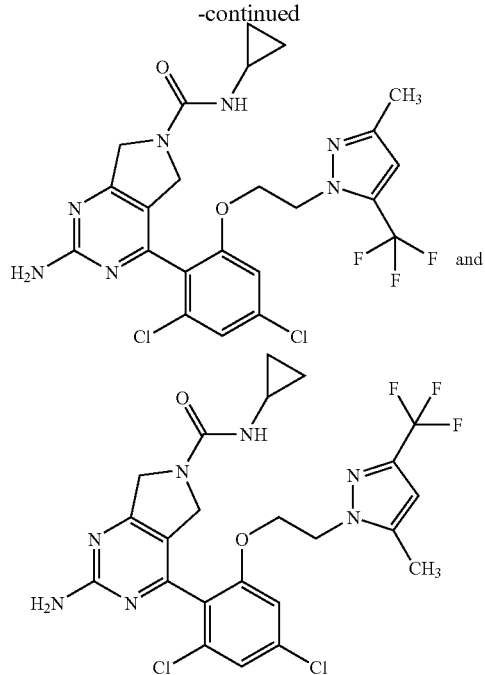
or a pharmaceutically acceptable salt thereof.
15. A compound of the formula
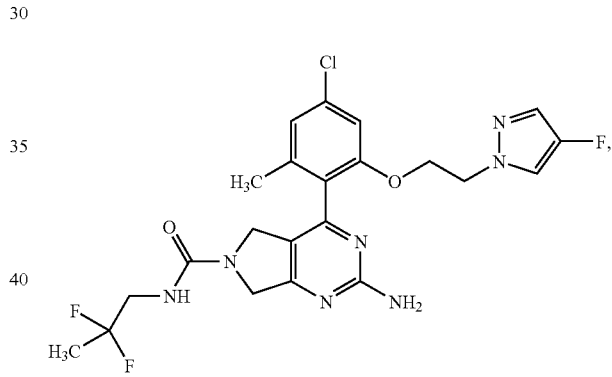
or a pharmaceutically acceptable salt thereof.
16. A pharmaceutical composition comprising the compound of claim 1, or a pharmaceutically acceptable salt thereof, and a pharmaceutically acceptable carrier.
* * * * *